US012742782B2

(12) United States Patent
Petty

(10) Patent No.: US 12,742,782 B2
(45) Date of Patent: Sep. 22, 2026

(54) METHODS OF DETERMINING RISK OF AND TREATING CANCER RECURRENCE

(71) Applicant: The Regents of the University of Michigan, Ann Arbor, MI (US)

(72) Inventor: Howard Petty, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 525 days.

(21) Appl. No.: 18/041,057

(22) PCT Filed: Aug. 11, 2021

(86) PCT No.: PCT/US2021/045570
§ 371 (c)(1),
(2) Date: Feb. 8, 2023

(87) PCT Pub. No.: WO2022/035978
PCT Pub. Date: Feb. 17, 2022

(65) Prior Publication Data

US 2023/0305014 A1 Sep. 28, 2023

Related U.S. Application Data

(60) Provisional application No. 63/064,152, filed on Aug. 11, 2020.

(51) Int. Cl.

| | |
|---|---|
| ***G01N 33/575*** | (2026.01) |
| ***A61K 31/165*** | (2006.01) |
| ***A61K 31/337*** | (2006.01) |
| ***A61P 35/00*** | (2006.01) |
| ***G01N 21/64*** | (2006.01) |
| ***G16H 50/20*** | (2018.01) |

(52) U.S. Cl.
CPC ..... *G01N 33/57595* (2026.01); *A61K 31/165* (2013.01); *A61K 31/337* (2013.01); *A61P 35/00* (2018.01); *G01N 21/6428* (2013.01); *G01N 21/6458* (2013.01); *G01N 2021/6439* (2013.01); *G01N 2333/9015* (2013.01); *G01N 2333/9104* (2013.01); *G01N 2333/914* (2013.01); *G16H 50/20* (2018.01)

(58) Field of Classification Search
CPC .......................... G01N 33/57496; A61P 35/00
See application file for complete search history.

(56) References Cited

U.S. PATENT DOCUMENTS

2003/0190602 A1* 10/2003 Pressman ............ C12Q 1/6809 435/5

FOREIGN PATENT DOCUMENTS

WO WO-2001058956 A2 8/2001

OTHER PUBLICATIONS

Grimm, M., Schmitt, S., Teriete, P. et al. A biomarker based detection and characterization of carcinomas exploiting two fundamental biophysical mechanisms in mammalian cells. BMC Cancer 13, 569 (2013). https://doi.org/10.1186/1471-2407-13-569 (Year: 2013).*
Chen, Weihua et al. "High RhoA expression at the tumor front in clinically localized prostate cancer and association with poor tumor differentiation." Oncology letters vol. 11,2 (2016): 1375-1381. doi:10.3892/ol.2015.4070 (Year: 2016).*
Wang, Ji et al. "Glucose transporter GLUT1 expression and clinical outcome in solid tumors: a systematic review and meta-analysis." Oncotarget vol. 8,10 (2017): 16875-16886. doi:10.18632/oncotarget.15171 (Year: 2017).*
Jans, Judith et al. "Expression and localization of hypoxia proteins in prostate cancer: prognostic implications after radical prostatectomy." Urology vol. 75,4 (2010): 786-92. doi:10.1016/j.urology.2009.08.024 (Year: 2010).*
Guo, Xinrong et al. "Re-Challenging Taxanes in Recurrent Breast Cancer in Patients Treated with (Neo-)Adjuvant Taxane-Based Therapy." Breast care (Basel, Switzerland) vol. 6,4 (2011): 279-283. doi:10.1159/000330946 (Year: 2011).*
https://web.archive.org/web/20171205100622/https://www.mayoclinic.org/diseases-conditions/recurrent-breast-cancer/diagnosis-treatment/drc-20377141#expand (Year: 2017).*
Murakami, Eriko et al. "Roles of Ras Homolog A in Invasive Ductal Breast Carcinoma." Acta histochemica et cytochemica vol. 49,5 (2016): 131-140. doi:10.1267/ahc.16020 (Year: 2016).*
Amar P., et al., "A Stochastic Automaton Shows How Enzyme Assemblies May Contribute to Metabolic Efficiency", BMC Systems Biology, Mar. 25, 2008, vol. 2, No. 27, pp. 1-13.
Anderson M.E., et al., "Transport and Direct Utilization of Gamma-Glutamylcyst(e)ine for Glutathione Synthesis", Proceedings of the National Academy of Sciences of the United States of America, Feb. 1983, vol. 80, No. 3, pp. 707-711.
Attanasio F., et al., "Novel Invadopodia Components Revealed by Differential Proteomic Analysis", European Journal of Cell Biology, Feb.-Mar. 2011, vol. 90, No. 2-3, pp. 115-127.
Babu E., et al., "Deletion of the Amino Acid Transporter Slc6a14 Suppresses Tumour Growth in Spontaneous Mouse Models of Breast Cancer", Biochemical Journal, Jul. 2015, vol. 469, No. 1, pp. 17-23.
Bansal A., et al., "Glutathione Metabolism in Cancer Progression and Treatment Resistance", Journal of Cell Biology, Jul. 2018, vol. 217, No. 7, pp. 2291-2298.
Bauler P., et al., "Channeling by Proximity: The Catalytic Advantages of Active Site Colocalization Using Brownian Dynamics", Journal of Physical Chemistry Letters, Apr. 9, 2010, vol. 1, pp. 1332-1335.
Boucher Y., et al., "Microvascular Pressure is the Principal Driving Force for Interstitial Hypertension in Solid Tumors: Implications for Vascular Collapse", Cancer Research, Sep. 15, 1992, vol. 52, No. 18, pp. 5110-5114.

(Continued)

*Primary Examiner* — Andrew D Kosar
*Assistant Examiner* — Connor K English
(74) *Attorney, Agent, or Firm* — David W. Staple; Casimir Jones, S.C.

(57) ABSTRACT

Provided herein are systems and methods for the prediction of recurrent cancer in a subject and systems and methods for using the prediction in the treatment or prevention of cancer recurrence.

9 Claims, 16 Drawing Sheets

(56) References Cited

OTHER PUBLICATIONS

Broders-Bondon F., et al., "Mechanotransduction in Tumor Progression: the Dark Side of the Force," Journal of Cell Biology, May 7, 2018, vol. 217, No. 5, pp. 1571-1587.
Buchner A., et al., "Clustering and Optimal Arrangement of Enzymes in Reaction-Diffusion Systems", Physical Review Letters, May 17, 2013, vol. 110, No. 20, 208104, pp. 1-8.
Campanella M.E., et al., "Assembly and Regulation of a Glycolytic Enzyme Complex on the Human Erythrocyte Membrane", Proceedings of the National Academy of Sciences of the United States of America, Feb. 15, 2005, vol. 102, No. 7, pp. 2402-2407.
Campbell I., "Chi-Squared and Fisher-Irwin Tests of Two-by-Two Tables with Small Sample Recommendations", Statistics in Medicine, Feb. 21, 2007, vol. 26, No. 19, pp. 3661-3675.
Castellana M., et al., "Enzyme Clustering Accelerates Processing of Intermediates Through Metabolic Channeling", Nature Biotechnology, Oct. 2014, vol. 32, No. 10, pp. 1011-1018 (10 pages).
Clark A. J., et al., "Identification of Lesion Subtypes in Biopsies of Ductal Carcinoma in Situ of the Breast Using Biomarker Ratio Imaging Microscopy", Scientific Reports, Jun. 1, 2016, vol. 6, No. 27039, pp. 1-6.
Clark A. J., et al., "Protocol for Biomarker Ratio Imaging Microscopy With Specific Application to Ductal Carcinoma in Situ of the Breast", Frontiers in Cell and Developmental Biology, Nov. 3, 2016, vol. 4, No. 120, pp. 1-9.
Coupel S., et al., "RhoA Activation Mediates Phosphatidylinositol 3-Kinase-Dependent Proliferation of Human Vascular Endothelial Cells: An Alloimmune Mechanism of Chronic Allograft Nephropathy", Journal of the American Society of Nephrology, Sep. 2004, vol. 15, No. 9, pp. 2429-2439.
Daum G., et al., "Association of Glycolytic Enzymes with the Cytoplasmic Side of the Plasma Membrane of Glioma Cells", Biochimica et Biophysica Acta, Apr. 1988, vol. 939, No. 2, pp. 277-281.
De Bock K., et al., "Role of PFKFB3-Driven Glycolysis in Vessel Sprouting", Cell, Aug. 1, 2013, vol. 154, No. 3, pp. 651-663.
Esserman L.J., et al., "Overdiagnosis And Overtreatment In Cancer: An Opportunity For Improvement", JAMA, Aug. 28, 2013, vol. 310, No. 8, pp. 797-798.
Estrela J.M., et al., "Glutathione in Cancer Biology and Therapy", Critical Reviews in Clinical Laboratory Sciences, 2006, vol. 43, No. 2, pp. 143-181.
Extended European Search Report for European Application No. 21856652.9, mailed Oct. 28, 2024, 15 Pages.
Fang J, et al., "Recurrent Prognostic Factors and Expression of GLUT-1, PI3K and p-Akt in Adenoid Cystic Carcinomas of the Head and Neck: Clinicopathological Features and Biomarkers of Adenoid Cystic Carcinoma," Oncology Letters, Jan. 1, 2012, vol. 4, No. 6, pp. 1234-1240, DOI: 10.3892/ol.2012.895, GR ISSN: 1792-1074, XP093182486. https://www.ncbi.nlm.nih.gov/pmc/articles/PMC3506780/pdf/01-04-06-1234.pdf.
Ferguson G., et al., "Glutamate Cysteine Ligase and the Age-Related Decline in Cellular Glutathione: The Therapeutic Potential of Gamma-Glutamylcysteine", Archives of Biochemistry and Biophysics, Mar. 2016, vol. 593, pp. 12-23.
Foldi M., et al., "Transketolase Protein TKTL1 Overexpression: A Potential Biomarker and Therapeutic Target in Breast Cancer", Oncology Reports, Apr. 2007, vol. 17, No. 4, pp. 841-845.
Glass-Marmor L., et al., "Taxol (Paclitaxel) Induces a Detachment of Phosphofructokinase from Cytoskeleton of Melanoma Cells and Decreases the Levels of Glucose 1,6-Bisphosphate, Fructose 1,6-Bisphosphate and ATP", European Journal of Pharmacology, Apr. 9, 1999, vol. 370, No. 2, pp. 195-199.
Goodison S., et al., "CD44 Cell Adhesion Molecules", Molecular Pathology, Aug. 1999, vol. 52, No. 4, pp. 189-196.
Guo Y-J., et al., "Potential Use of Soluble CD44 in Serum as Indicator of Tumor Burden and Metastasis in Patients with Gastric or Colon Cancer", Cancer Research, Jan. 15, 1994, vol. 54, No. 2, pp. 422-426.
Hanna W.M., et al., "Ductal Carcinoma in Situ of the Breast: An Update for the Pathologist in the Era of Individualized Risk Assessment and Tailored Therapies", Modern Pathology, Jul. 2019, vol. 32, No. 7, pp. 896-915.
Harding C., et al., "Breast Cancer Screening, Incidence, And Mortality Across US Counties", JAMA Internal Medicine, Sep. 2015, vol. 175, No. 9, pp. 1483-1489.
Hayat M.A., "Stains and Cytochemical Methods", Plenum Press, 1993, TOC only, 11 pages.
Heo J., et al., "Redox Regulation of RhoA", Biochemistry, Dec. 2006, vol. 45, No. 48, pp. 14481-14489.
Hinzpeter F., et al., "Optimal Compartmentalization Strategies for Metabolic Microcompartments", Biophysical Journal, Feb. 28, 2017, vol. 112, No. 4, pp. 767-779.
Holt L.J., et al., "Domain Antibodies: Proteins for Therapy," Trends in Biotechnology, Nov. 2003, vol. 21, No. 11, pp. 484-490.
Huang J-B., et al., "Transaldolase is Part of a Supramolecular Complex Containing Glucose-6-Phosphate Dehydrogenase in Human Neutrophils that Undergoes Retrograde Trafficking During Pregnancy", Metabolism, Aug. 2005, vol. 54, No. 8, pp. 1027-1033.
International Search Report and Written Opinion for International Application No. PCT/US2021/045570, mailed Nov. 22, 2021, 10 Pages.
Ishimoto T., et al., "CD44 Variant Regulates Redox Status in Cancer Cells by Stabilizing the xCT Subunit of System xc- and Thereby Promotes Tumor Growth", Cancer Cell, Mar. 15, 2011, vol. 19, No. 3, pp. 387-400.
Jain M., et al., "Glucose-6-Phosphate Dehydrogenase Modulates Cytosolic Redox Status and Contractile Phenotype in Adult Cardiomyocytes", Circulation Research, Jul. 25, 2003, vol. 93, No. 2, e9-e16, pp. 1-8.
Jeong D., et al., "RhoA Is Associated with Invasion and Poor Prognosis in Colorectal Cancer", International Journal of Oncology, Feb. 2016, vol. 48, No. 2, pp. 714-722.
Ju H-Q., et al., "Disrupting G6PD-Mediated Redox Homeostasis Enhances Chemosensitivity in Colorectal Cancer", Oncogene, Nov. 2017, vol. 36, No. 45, pp. 6282-6292.
Kaira K., et al., "Prognostic Significance of L-Type Amino-Acid Transporter 1 Expression in Surgically Resected Pancreatic Cancer", British Journal of Cancer, Aug. 7, 2012, vol. 107, No. 4, pp. 632-638.
Kajita M., et al., "Membrane-Type 1 Matrix Metalloproteinase Cleaves CD44 and Promotes Cell Migration", The Journal of Cell Biology, May 28, 2001, vol. 153, No. 5, pp. 893-904.
Kapuscinski J., "DAPI: A DNA-Specific Fluorescent Probe", Biotechnic & Histochemistry, Sep. 1995, vol. 70, No. 5, pp. 220-233.
Keller J., et al., "Muscarinic Receptor-Stimulated Cytosol-Membrane Translocation of RhoA", FEBS Letters, Feb. 1997, vol. 403, No. 3, pp. 299-302.
Kindzelskii A.L., et al., "6-Phosphogluconate Dehydrogenase and Glucose-6-Phosphate Dehydrogenase Form a Supramolecular Complex in Human Neutrophils that Undergoes Retrograde Trafficking During Pregnancy", The Journal of Immunology, May 15, 2004, vol. 172, No. 10, pp. 6373-6381.
Kindzelskii A.L., et al., "Pregnancy Alters Glucose-6-Phosphate Dehydrogenase Trafficking, Cell Metabolism and Oxidant Release Of Maternal Neutrophils", Journal of Clinical Investigation, Dec. 2002, vol. 110, No. 12, pp. 1801-1811.
Kobayashi K., et al., "Clinical Significance of CD44 Variant 9 Expression as a Prognostic Indicator in Bladder Cancer", Oncology Reports, Nov. 2016, vol. 36, No. 5, pp. 2852-2860.
Kraft A.M., et al., "Spatial Locations of Certain Enzymes and Transporters Within Preinvasive Ductal Epithelial Cells Predict Human Breast Cancer Recurrences," American Journal of Physiology Cell Physiology, Sep. 9, 2020, vol. 319, No. 5, pp. C910-C921, DOI: 10.1152/ajpcell.00280.2020, XP093021522.
Kusama T., et al., "Inhibition of Epidermal Growth Factor-Induced RhoA Translocation and Invasion of Human Pancreatic Cancer Cells by 3-Hydroxy-3-Methylglutaryl-Coenzyme A Reductase Inhibitors", Cancer Research, Jun. 2001, vol. 61, No. 12, pp. 4885-4891 (8 Pages).

(56) References Cited

OTHER PUBLICATIONS

Le Gal K., et al., "Antioxidants Can Increase Melanoma Metastasis in Mice", Science Translational Medicine, Oct. 7, 2015, vol. 7, No. 308, 308re8, 8 Pages.

Lee E.E., et al., "A Protein Kinase C Phosphorylation Motif in GLUT1 Affects Glucose Transport and is Mutated in GLUT1 Deficiency Syndrome", Molecular Cell, Jun. 4, 2015, vol. 58, No. 5, pp. 845-853, DOI: 10.1016/j.molcel.2015.04.015, ISSN: 1097-2765, XP029171308.

Lochman P., et al., "High-Throughput Capillary Electrophoretic Method for Determination of Total Aminothiols in Plasma and Urine", Electrophoresis, Apr. 2003, vol. 24, No. 7-8, pp. 1200-1207.

Marshall E., "Dare to Do Less", Breast Cancer, Science, Mar. 28, 2014, vol. 343, No. 6178, pp. 1454-1456.

Massey A.R., et al., "Increased RhoA Translocation in Renal Cortex of Diabetic Rats", Life Sciences, May 16, 2003, vol. 72, No. 26, pp. 2943-2952.

O'Connor K.L., et al., "Dynamic Functions of RhoA in Tumor Cell Migration and Invasion", Small GTPases, Jul. 2013, vol. 4, No. 3, pp. 141-147.

Pardo-Pastor C., et al., "Piezo2 Channel Regulates RhoA and Actin Cytoskeleton to Promote Cell Mechanobiological Responses", Proceedings of the National Academy of Sciences of the United States of America, Feb. 20, 2018, vol. 115, No. 8, pp. 1925-1930.

Partial Supplementary European Search Report for European Application No. 21856652.9, mailed Aug. 7, 2024, 15 Pages.

Richman P.G., et al., "Regulation of Gamma-Glutamyl-Cysteine Synthetase by Nonallosteric Feedback Inhibition by Glutathione", The Journal of Biological Chemistry, Feb. 25, 1975, vol. 250, No. 4, pp. 1422-1426.

Saito T., et al., "The Precision-Recall Plot is More Informative than the ROC Plot When Evaluating Binary Classifiers On Imbalanced Datasets", PLoS One, Mar. 4, 2015, vol. 10, No. 3, e0118432, pp. 1-21.

Schwartz D., et al., "Detachment of the Glycolytic Enzymes, Phosphofructokinase and Aldolase, From Cytoskeleton of Melanoma Cells, Induced by Local Anesthetics", Molecular Genetics and Metabolism, Feb. 2000, vol. 69, No. 2, pp. 159-164.

Shimizu K., et al., "ASC Amino-Acid Transporter 2 (ASCT2) as a Novel Prognostic Marker in Non-Small Cell Lung Cancer", British Journal of Cancer, Apr. 15, 2014, vol. 110, No. 8, pp. 2030-2039.

Shorten C., et al., "Text Data Augmentation for Deep Learning", Journal of Big Data, 2021, vol. 8, No. 101, pp. 1-34.

Stanton R.C., et al., "Rapid Release of Bound Glucose-6-Phosphate Dehydrogenase by Growth Factors. Correlation With Increased Enzymatic Activity", The Journal of Biological Chemistry, Jul. 5, 1991, vol. 266, No. 19, pp. 12442-12448.

Stanton R.C., "Glucose-6-Phosphate Dehydrogenase, NADPH, and Cell Survival", IUBMB Life, May 2012, vol. 64, No. 5, pp. 362-369.

Stark A-A., et al., "The Role of Gamma-Glutamyl Transpeptidase in the Biosynthesis of Glutathione", Biofactors, 2003, vol. 17, No. 1-4, pp. 139-149.

Sun K., et al., "Oxidized ATM-Mediated Glycolysis Enhancement in Breast Cancer-Associated Fibroblasts Contributes to Tumor Invasion Through Lactate as Metabolic Coupling," EBioMedicine, NL , Mar. 1, 2019, vol. 41, pp. 370-383, DOI: 10.1016/j.ebiom.2019.02.025, ISSN: 2352-3964, XP093184183, abstract, figure 4, https://www.sciencedirect.com/science/article/pii/S2352396419300970.

The Alpha-Tocopherol., "The Effect of Vitamin E and Beta Carotene on the Incidence of Lung Cancer and Other Cancers in Male Smokers", The New England Journal of Medicine, Beta Carotene Cancer Prevention Study Group, Apr. 14, 1994, vol. 330, No. 15, pp. 1029-1035.

Tian W-N., et al., "Signal Transduction Proteins that Associate with the Platelet-Derived Growth Factor (PDGF) Receptor Mediate the PDGF-Induced Release of Glucose-6-Phosphate Dehydrogenase From Permeabilized Cells", The Journal of Biological Chemistry, May 20, 1994, vol. 269, No. 20, pp. 14798-14805.

Uyeda K., "Interactions of Glycolytic Enzymes With Cellular Membranes", Current Topics in Cellular Regulation, Jan. 1992, vol. 33, pp. 31-46.

Van Geldermalsen M., et al., "ASCT2/SLC1A5 Controls Glutamine Uptake and Tumour Growth in Triple-Negative Basal-Like Breast Cancer", Oncogene, Jun. 16, 2016, vol. 35, No. 24, pp. 3201-3208.

Von Hippel P.H., et al., "Facilitated Target Location in Biological Systems", The Journal of Biological Chemistry, Jan. 15, 1989, vol. 264, No. 2, pp. 675-678.

Wang M., et al., "Protein Prenylation: Unique Fats Make Their Mark on Biology", Nature Reviews Molecular Cell Biology, Feb. 2016, vol. 17, No. 2, pp. 110-122.

Weed D.T., et al., "FOXP3 Subcellular Localization Predicts Recurrence in Oral Squamous Cell Carcinoma," PLOS ONE, US, Aug. 20, 2013, vol. 8, No. 8: e71908, 8 Pages, DOI: 10.1371/journal.pone.0071908, ISSN: 1932-6203, XP093180896, the Whole Document [Retrieved on Dec. 4, 2020].

Wellberg E.A., et al., "The Glucose Transporter GLUT1 is Required for ErbB2-Induced Mammary Tumorigenesis", Breast Cancer Research, Dec. 20, 2016, vol. 18, No. 1, 131, pp. 1-15.

Wilkinson E.J., et al., "Probability in Lymph Node Sectioning", Cancer, May 1974, vol. 33, No. 5, pp. 1269-1274.

Wu C., et al., "Simultaneous Targeting of Multiple Disease Mediators by a Dual-Variable-Domain Immunoglobulin", Nature Biotechnology, Nov. 2007, vol. 25, No. 11, pp. 1290-1297.

Xu I.M-J., et al., "Transketolase Counteracts Oxidative Stress to Drive Cancer Development", Proceedings of the National Academy of Sciences of the United States of America, Jan. 25, 2016, vol. 113, No. 6, pp. E725-E734.

Zala D., et al., "Vesicular Glycolysis Provides On-Board Energy for Fast Axonal Transport", Cell, Jan. 31, 2013, vol. 152, No. 3, pp. 479-491.

Zarka M.H., et al., "Oral Administration of Gamma-Glutamylcysteine Increases Intracellular Glutathione Levels above Homeostasis in a Randomised Human Trial Pilot Study", Redox Biology, Apr. 2017, vol. 11, pp. 631-636.

Zhang C., et al., "Tumour-Associated Mutant p53 Drives the Warburg Effect", Nature Communications, 2013, vol. 4, No. 2935, pp. 1-33.

* cited by examiner

FIG. 11

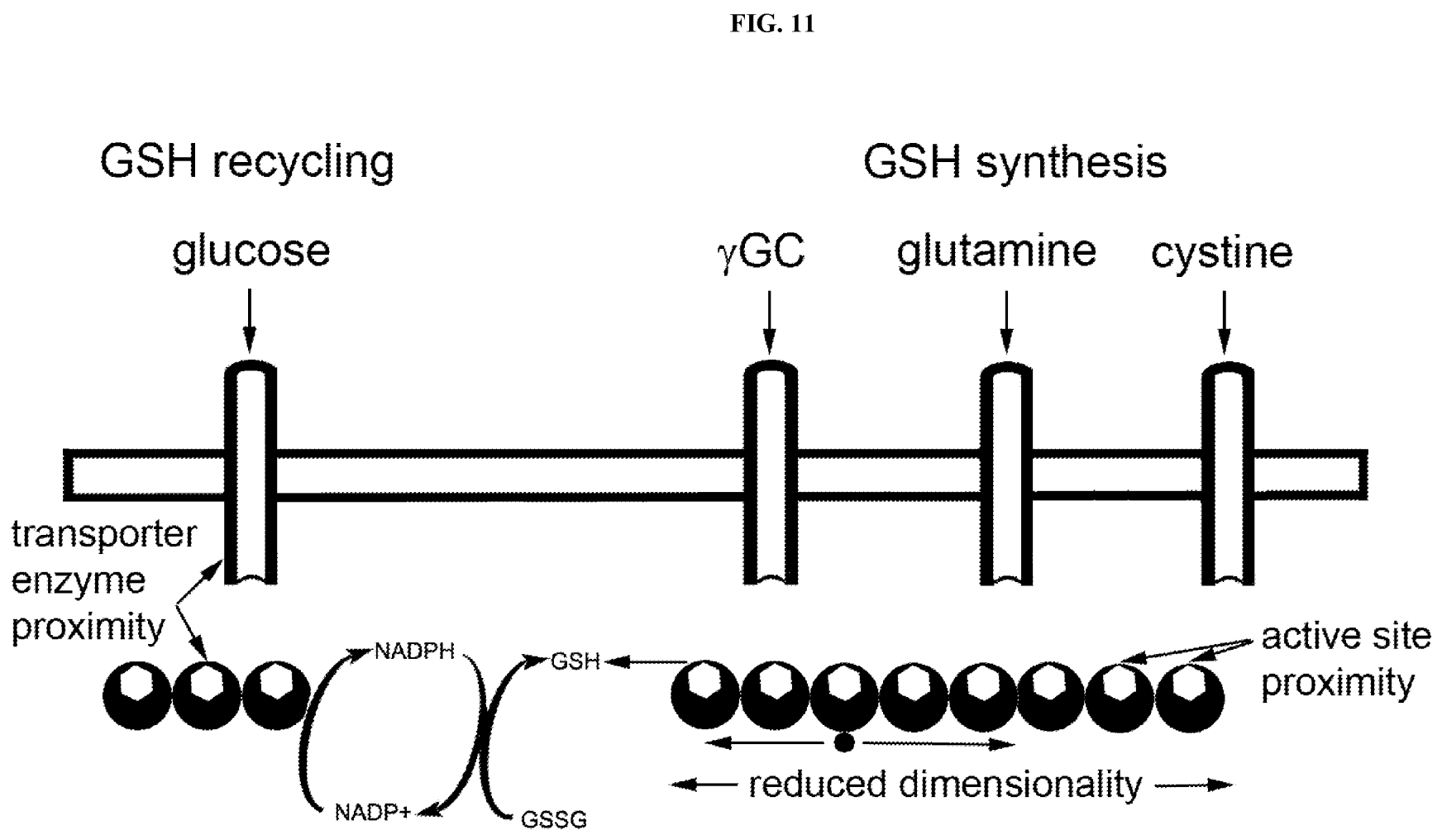

GSH recycling
glucose
GSH synthesis
γGC
glutamine
cystine
active site proximity
reduced dimensionality
GSH
GSSG
NADPH
NADP+
transporter enzyme proximity

METHODS OF DETERMINING RISK OF AND TREATING CANCER RECURRENCE

FIELD

The present disclosure provides systems and methods for the prediction and treatment of recurrent cancer in a subject.

BACKGROUND

Ductal carcinoma in situ (DCIS) of the breast is a common non-invasive cancer. Epidemiology studies suggest that indolent and aggressive forms of DCIS exist (Ref 1-3; incorporated by reference in their entireties), with the aggressive form potentially leading to life-threatening disease. The two presumed forms of DCIS would exhibit cellular proliferation (indolent) or cellular proliferation plus biochemical and biophysical changes to support invasive behavior (aggressive). Some patients treated for ductal carcinoma in situ (DCIS) of the breast will experience cancer recurrences, whereas other patients will not. Unfortunately, current techniques cannot identify which pre-invasive lesions will lead to recurrent cancer. Although screening tools can detect cancer, they cannot predict cancer recurrences.

SUMMARY

Experiments conducted during development of embodiments herein demonstrate that phosphophorylated glucose transporter type 1, transketolase-like protein-1, glutathione synthetase, GTP-loaded RhoA, and RhoA accumulate at the ductal epithelial cell periphery in biopsies of women who will suffer recurrences DCIS, but not in samples from women who will not experience recurrences. Using machine learning/vision augments the prediction of recurrent and non-recurrent patient outcomes using fluorescence micrographs of tissue sections. In some embodiments, provided herein are systems and methods that distinguish or predict recurrent cancer from non-recurrent cancer.

In some embodiments, the methods comprise determining intracellular localization of at least one biomarker for cancer recurrence in a sample comprising cancer cells from a subject and predicting cancer recurrence in a subject. In some embodiments, the peripheral intracellular localization of at least one biomarker predicts cancer recurrence. In some embodiments, the methods further comprise a) immunostaining the sample with a primary antibody directed to the biomarker for cancer recurrence and b) imaging the sample. In some embodiments, the primary antibody is detected with a secondary antibody comprising a detectable label. In some embodiments, imaging the sample comprises fluorescence microscopy.

The biomarker for cancer recurrence may comprise an enzyme or transporter involved in glutathione cycle. In some embodiments, the enzyme or transporter involved in glutathione cycle is selected from the group consisting of: phosphorylated glucose transporter type 1; transketolase-like protein-1; glutathione synthetase; GTP-loaded RhoA; RhoA; and any combination thereof.

The cancer may be breast cancer, prostate cancer, lung cancer, melanoma, kidney cancer, thyroid cancer, pancreatic cancer, stomach cancer or bladder cancer. In some embodiments, the breast cancer comprises ductal carcinoma in situ of the breast, lobular carcinoma in situ, atypical ductal hyperplasia, or atypical lobular hyperplasia. In select embodiments, the cancer recurrence is ipsilateral breast cancer recurrence. In select embodiments, the sample comprises a formalin-fixed paraffin-embedded cancer tissue sample or a cancer metastases tissue or cell sample.

In some embodiments, the methods further comprise treating a subject predicted to have cancer recurrence. The treatment may include surgery or administration of inhibitors to enzyme or transporter accumulation at plasma membrane. In some embodiments, the inhibitors to enzyme accumulation at plasma membrane comprise colchicine, taxol, a calmodulin antagonist, a prenylation inhibitor, an anesthetic, or combinations thereof.

Provided herein are methods of preventing cancer recurrence in a subject comprising predicting cancer recurrence by the methods disclosed herein and administering a treatment regimen. The treatment regimen may comprise one or more of surgery; administration of an inhibitor(s) to enzyme or transporter accumulation at plasma membrane; immunotherapy; radiotherapy; and administration of a chemotherapeutic agent(s).

Also provided herein are methods for distinguishing recurrent from non-recurrent cancer comprising determining intracellular localization of a biomarker for cancer recurrence in a sample comprising cancer cells, wherein the biomarker for cancer recurrence is selected from the group consisting of: phosphorylated glucose transporter type 1; transketolase-like protein-1; glutathione synthetase; GTP-loaded RhoA; RhoA; and any combination thereof. In some embodiments, the peripheral intracellular localization of the biomarker for cancer recurrence indicates recurrent cancer.

Further disclosed herein a systems for use in predicting cancer recurrence or distinguishing between recurrent and non-recurrent cancer. The systems comprise at least one or all of a primary antibody to a biomarker for cancer recurrence; an imaging instrument; software configured to determine the intracellular location of the biomarker for cancer recurrence and a sample.

In some embodiments, provided herein are methods comprising: (a) obtaining a sample from a subject; and (b) determining intracellular localization of one or more biomarkers selected from phosphorylated glucose transporter type 1, transketolase-like protein-1, glutathione synthetase, GTP-loaded RhoA, and RhoA in cells from the sample. In some embodiments, methods further comprise determining intracellular localization of one or more additional biomarkers in the cells of the sample. In some embodiments, the subject has cancer or has previously had cancer, and wherein peripheral intracellular localization of the one or more predicts cancer recurrence. In some embodiments, determining intracellular localization comprises: immunostaining the sample with a primary antibody directed to the biomarker for cancer recurrence; and imaging the sample. In some embodiments, the primary antibody is detected with a secondary antibody comprising a detectable label. In some embodiments, imaging the sample comprises fluorescence microscopy. In some embodiments, the cancer is selected from breast cancer, prostate cancer, lung cancer, melanoma, kidney cancer, thyroid cancer, pancreatic cancer, stomach cancer or bladder cancer. In some embodiments, the breast cancer comprises ductal carcinoma in situ of the breast, lobular carcinoma in situ, atypical ductal hyperplasia, or atypical lobular hyperplasia. In some embodiments, the cancer recurrence is ipsilateral breast cancer recurrence. In some embodiments, the sample comprises a formalin-fixed paraffin-embedded cancer tissue sample or a cancer metastases tissue or cell sample. In some embodiments, methods further comprise treating a subject predicted to have cancer recurrence with surgery. In some embodiments, methods further comprise treating a subject predicted to have cancer recurrence with administration of inhibitors to enzyme or transporter accumulation at plasma membrane. In some embodiments, the inhibitors to enzyme accumulation at plasma membrane comprise colchicine, taxol, a calmodulin antagonist, a prenylation inhibitor, an anesthetic, or combinations thereof.

BRIEF DESCRIPTION OF THE DRAWINGS

FIG. 10A shows the precision and recall curves using a training dataset based upon the peripheral accumulation of biomarkers to identify samples that will be associated with future recurrences. FIG. 10B shows a second pair of precision and recall curves for a second training dataset based upon the dataset plus holdout controls followed by minimal additional editing.

FIG. 11 is a schematic of the physio-chemical advantages of enzyme trafficking. The formation of pen-membrane enzyme regions is expected to have significant effects on the kinetics of GSH formation. As the enzyme-rich regions are adjacent to the plasma membrane, the distance between transport proteins and enzymes is minimized. As these enzymes are near one-another, the proximity of their active sites will also increase the rate of GSH formation. Free substrate molecules in the pen-membrane space can adsorb to the enzymes, followed by diffusion in one or two dimensions, which will also increase reaction kinetics.

DEFINITIONS

Figure 1:
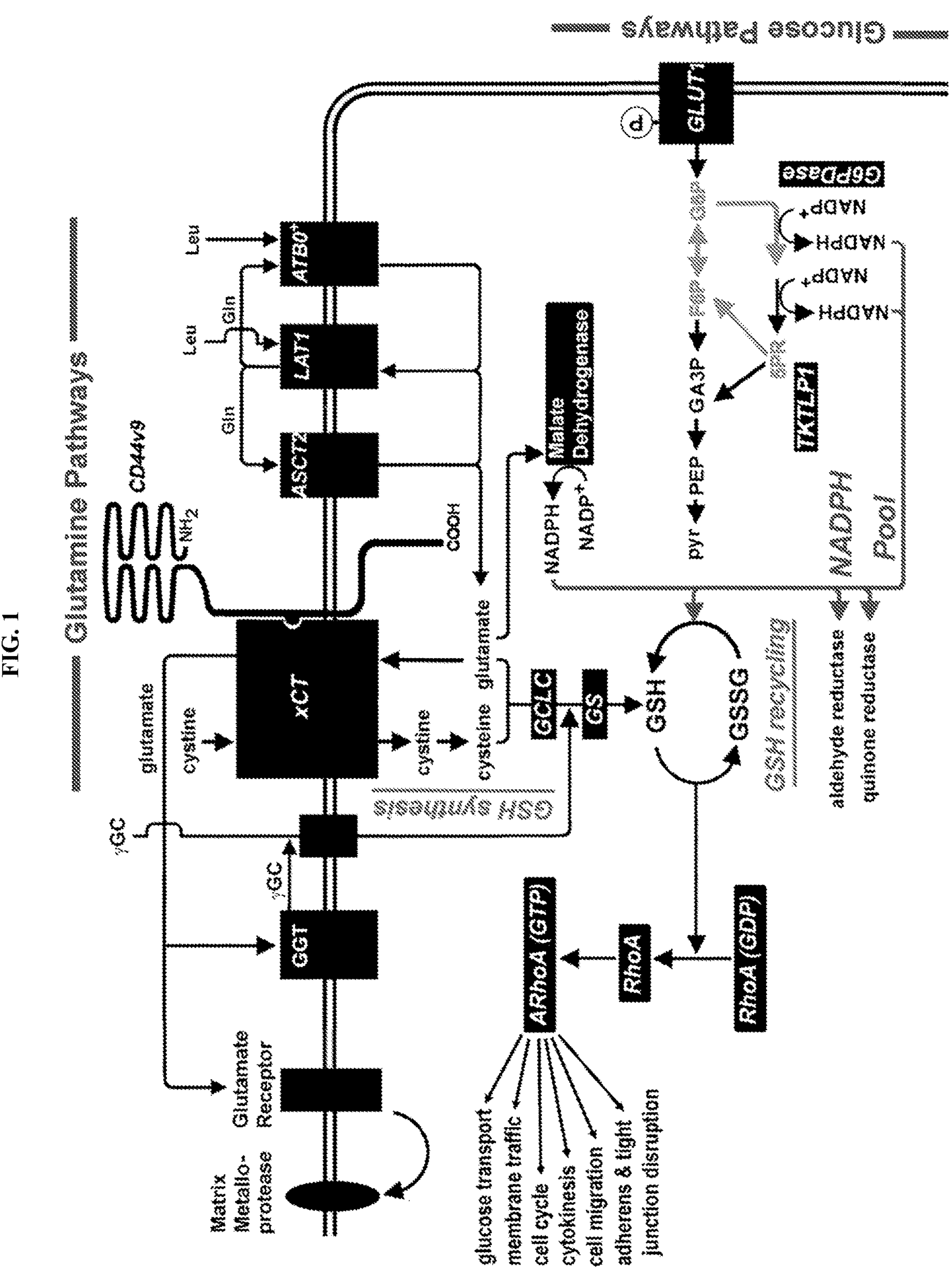
FIG. 1 is a schematic of biomarkers and pathways identified herein. These biomarkers promote: 1) Glutathione Assembly: glutamate cysteine ligase catalytic domain (GCLC), glutathione synthetase (GS), cystine-glutamate antiporter (xCT), CD44v9, glutamine uptake (ASCT2, ATBO+, LAT1), and leucine uptake (LAT1), g-glutamyl transpeptidase (GGT) and the metabolite gamma-glutamyl cysteine (gGC), 2) The pentose-phosphate pathway: glucose transporter 1 (GLUT1), glucose 6-phosphate dehydrogenase (G6PD), transketolase (TKT), transketolase-like protein 1 (TKTLP1), and 3) Signaling Pathways: RhoA, RhoA with bound GTP and CD74.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of" the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein, the terms "administering," "providing", and "introducing," are used interchangeably herein and refer to the placement of therapeutic agents into a subject by a method or route which results in at least partial localization a desired site. The therapeutic agents can be administered by any appropriate route which results in delivery to a desired location in the subject.

"Antibody" and "antibodies," as used herein, refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, $F(ab')_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology,* 25(11): 1290-1297 (2007) and PCT International Application WO 2001/058956, the contents of each of which are herein incorporated by reference), or domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nobodies, VHH, or other domain structure), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2).

As used herein, the term "biomarker" refers to a substance, the detection of which indicates a particular disease/condition or risk of acquiring/having a particular disease/condition. In the context of the method described herein, a "biomarker" can be a protein (e.g. an enzyme or transporter) that changes location with a cell as a predictor of cancer recurrence or an indicator of recurrent cancer.

As used herein, the term "chemotherapeutic" or "anti-cancer drug" includes any drug used in cancer treatment or any radiation sensitizing agent. Chemotherapeutics may include alkylating agents (including, but not limited to, cyclophosphamide, mechlorethamine, chlorambucil, melphalan, dacarbazine, nitrosoureas, and temozolomide), anthracyclines (including, but not limited to, daunorubicin, doxorubicin, epirubicin, idarubicin, mitoxantrone, and valrubicin), cytoskeletal disrupters or taxanes (including, but not limited to, paclitaxel, docetaxel, abraxane, and taxotere), epothilones, histone deacetylase inhibitors (including, but not limited to, vorinostat and romidepsin), topoisomerase inhibitors (including, but not limited to, irinotecan, topotecan, etoposide, teniposide, and tafluposide), kinase inhibitors (including, but not limited to, bortezomib, erlotinib, gefitinib, imatinib, vemurafenib, and vismodegib), nucleotide analogs and precursor analogs (including, but not limited to, azacitidine, azathioprine, capecitabine, cytarabine, doxifluridine, fluorouracil, gemcitabine, hydroxyurea, mercaptopurine, methotrexate, and tioguanine), peptide antibiotics (including, but not limited to, bleomycin and actinomycin), platinum-based agents (including, but not limited to, carboplatin, cisplatin and oxaliplatin), retinoids (including, but not limited to, tretinoin, alitretinoin, and bexarotene), vinca alkaloids and derivatives (including, but not limited to, vinblastine, vincristine, vindesine, and vinorelbine), or combinations thereof. The chemotherapeutic may in any form necessary for efficacious administration and functionality. "Chemotherapy" designates a therapeutic regimen which includes administration of a "chemotherapeutic" or "anti-cancer drug."

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

The terms "sample," "biological sample," and "test sample" are used interchangeably herein to refer to any material, biological fluid, tissue, or cell obtained or otherwise derived from an individual. The term sample also includes materials derived from a tissue culture or a cell culture. This includes blood (including whole blood, leukocytes, peripheral blood mononuclear cells, buffy coat, plasma, and serum), mucosal biopsy tissue and brushed cells, sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate (e.g., bronchoalveolar lavage), bronchial brushing, synovial fluid, joint aspirate, organ secretions, cells, a cellular extract, and cerebrospinal fluid. This also includes experimentally separated fractions of all of the foregoing. For example, a blood sample can be fractionated into serum, plasma, or into fractions containing particular types of blood cells, such as red blood cells or white blood cells (leukocytes). Any suitable methods for obtaining a sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, pancreas, and liver. Samples can also be collected, e.g., by micro dissection (e.g., laser capture micro dissection (LCM) or laser micro dissection (LMD)), bladder wash, smear (e.g., a PAP smear), or ductal lavage. A sample obtained or derived from an individual includes any such sample that has been processed in any suitable manner after being obtained from the individual. It will be appreciated that obtaining a biological sample from a subject may comprise extracting the sample directly from the subject or receiving the sample from a third party. In the context of the method described herein, the sample comprises cells.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, "treat," "treating" and the like means a slowing, stopping or reversing of progression of a disease or disorder. The term also means a reversing of the progression of such a disease or disorder. As such, "treating" means an application or administration of the methods or agents described herein to a subject, where the subject has a disease or a symptom of a disease, where the purpose is to cure, heal, alleviate, relieve, alter, remedy, ameliorate, improve or affect the disease or symptoms of the disease.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

DETAILED DESCRIPTION

Prior available techniques are unable to predict breast cancer recurrences using early, pre-invasive lesions. In some embodiments, provided herein are methodologies comprising imaging, computer vision, and conventional pathology samples to predict patient outcomes. Experiments conducted during development of embodiments herein demonstrate that the spatial locations of several enzymes and transporters influencing the glutathione cycle are key determinants of cancer recurrences. These proteins accumulate at the periphery of cancer cells in instances where cancer recurrence is a high risk. It is contemplated that these proteins heighten the metabolic flux of reduced glutathione. High levels of precision and recall were noted for the binary classification of patient outcomes.

Experiments suggest that intracellular reducing conditions promote cancer metastases (Refs. 4-6; incorporated by reference in their entireties). Experiments were conducted during development of embodiments herein to determine whether GSH-sensitive RhoA GTPases (Ref 7; incorporated by reference in its entirety), GSH synthesis enzymes, and elements of the pentose-phosphate pathway (PPP) accumulate at the epithelial cell periphery in recurrent, but not non-recurrent, DCIS. Experiments analyzed the PPP, glucose, glutamine and cystine transport, and the glutathione (GSH) synthesis pathway to find changes that correlate with cancer recurrences (FIG. 1). Transport proteins promoting GSH synthesis are the cystine-glutamate antiporter SLC7A11 (xCT); the glutamine transporter SLC1A5 (ASCT2—alanine, serine, cysteine transporter), the sodium/chloride-dependent amino acid transporter SLC6A14 (ABT0+), and the large neutral amino acid transporter SLC7A5 (LAT1) (Refs. 8-13; incorporated by reference in their entireties). Glutamate-cysteine ligase catalytic domain (GCLC) and γ-glutamyl transpeptidase (GGT) catalyze γ-glutamyl-cysteine (γGC) synthesis, the substrate for glutathione synthetase (GS) (Refs. 6, 14; incorporated by reference in their entireties). Oxidized glutathione (GSSG) is reduced to GSH via NADPH provided by the PPP. The rate-controlling step of the PPP's oxidative arm is catalyzed by glucose 6-phosphate dehydrogenase (G6PD) (Ref 15; incorporated by reference in its entirety). The rate-controlling step of the PPP's non-oxidative arm is mediated by transketolase (TLT) and its oncogenic form, transketolase-like protein-1 (TKTLP1) (Ref 16; incorporated by reference in its entirety). Glucose transporter type 1 (GLUT1) promotes breast cancer cell metabolism (Refs. 18, 19; incorporated by reference in their entireties). RhoA, another predictor of poor patient outcomes, participates in cancer cell metabolism and invasiveness (Refs. 20, 21; incorporated by reference in their entireties). The activities of these proteins are influenced by: isotype switching, expression level, phosphorylation, intracellular trafficking, GTP binding, GSH concentration, assembly into supramolecular complexes, substrate availability, and feedback/feed-forward mechanisms.

Experiments were conducted during development of embodiments herein to determine if a role exists for enzyme and transporter trafficking in cancer recurrences and non-recurrences of DCIS patients.

Although enzyme trafficking is one of the least studied regulatory pathways, it plays key roles in glycolysis, membrane transport, and cellular redox status. Previous studies found glycolytic enzyme accumulation at plasma membranes and cytoskeletons (Refs. 22-24; incorporated by reference in its entirety), which can be dissociated by taxol, phosphorylation, and calmodulin antagonists (Ref 25; incorporated by reference in its entirety). PPP enzymes also interact with plasma membranes, which can be regulated by growth factors (Refs. 26, 27; incorporated by reference in their entireties). Heightened G6PD activity at the plasma membrane of fertilized eggs affords protection from oxidative damage during oxidative crosslinking of the outer coat (Ref 28; incorporated by reference in its entirety). A similar protective response has been reported for G6PD trafficking in cardiomyocytes (Ref 29; incorporated by reference in its entirety). The PPP enzymes G6PD, 6-phosphogluconate dehydrogenase (6PGD), and transaldolase traffic to the periphery of normal peripheral blood neutrophils, but during pregnancy these enzymes localize near the neutrophil's centrosomes (Refs. 30-32; incorporated by reference in their entireties). The centrosomal accumulation of PPP enzymes reduces NADPH levels and NADPH oxidase-mediated oxidant production, presumably to protect the fetus from these inflammatory cells (Refs. 30-32; incorporated by reference in their entireties). Enzyme accumulation near membranes promotes monomer catalysis, local product synthesis, and protects enzymes from inactivation (Ref 24; incorporated by reference in its entirety). It is suggested that enzyme clustering increases product flux (Refs. 33, 34; incorporated by reference in their entireties). Accumulation of specific enzymes and transporters at the cell periphery provide incoming substrates (glucose, cysteine, glutamine, γGC) preferential access to catalytic steps at the cell periphery. Moreover, the reduction in dimensionality of peri-membrane enzymes enhances product formation (Refs. 35, 36; incorporated by reference in their entireties), because adsorbed substrates diffuse in restricted dimensions before reacting. Using antibodies directed against these enzymes and transporters and certain of their modified forms as well as formalin-fixed paraffin-embedded (FFPE) human pathology samples, experiments were conducted during development of embodiments herein to investigate the intracellular locations of certain molecules promoting GSH synthesis or responding to GSH levels in recurrent and non-recurrent disease.

Experiments conducted during development of embodiments herein demonstrate that RhoA, RhoA(GTP), phospho-GLUT1, GS, and TKTLP1 collect near plasma membranes of ductal epithelial cells prior to cancer recurrences, but not in samples from recurrence-free patients. The disclosed method provides a prognostic test to classify DCIS biopsies as recurrent or non-recurrent. Experiments determined that the expression levels of these proteins did not correlate with recurrence, but the locations of these enzymes and transporters were highly predictive of patient outcomes.

Figure 8:
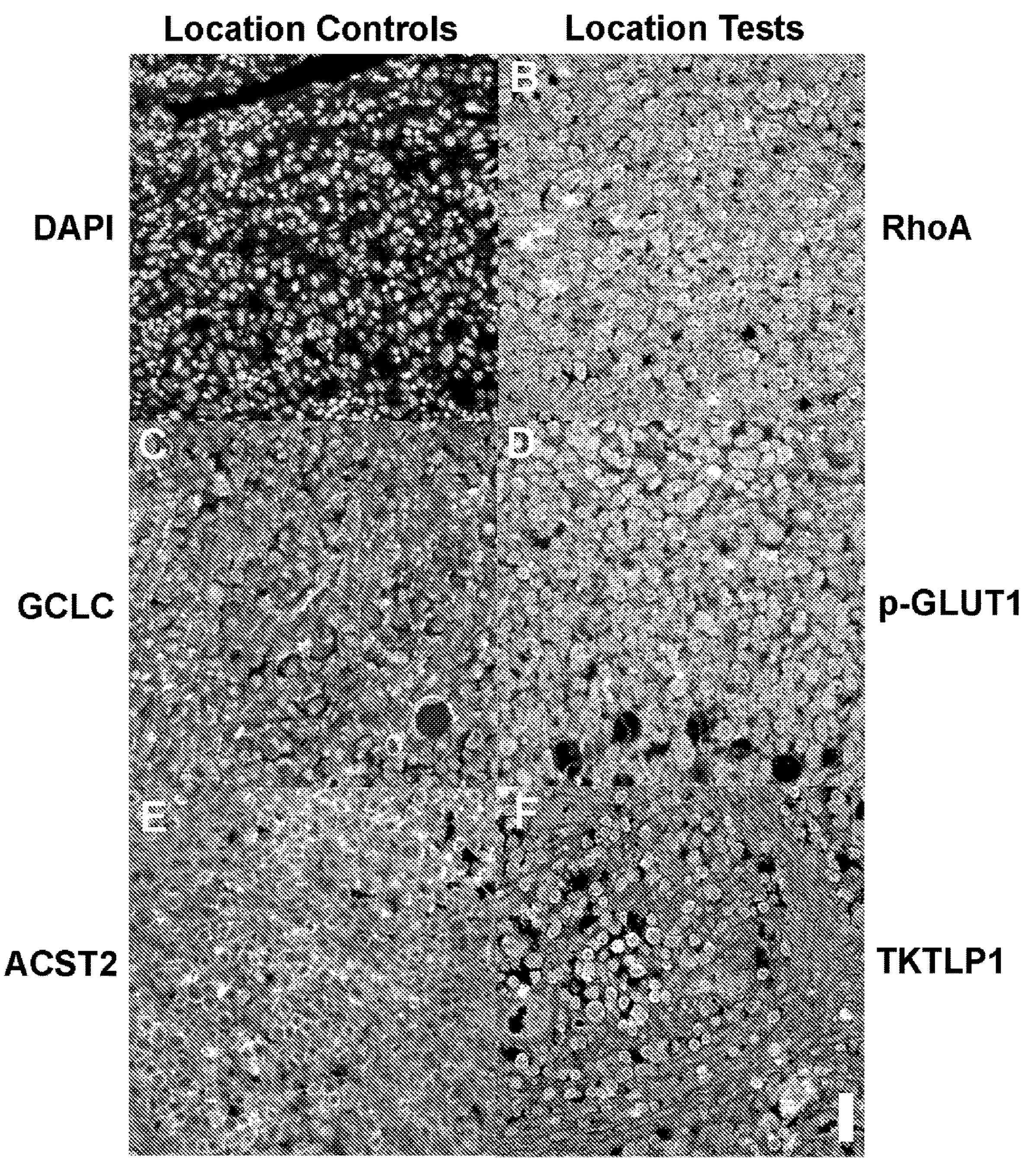
FIG. 8 is micrographs of a sample of breast cancer metastases to the omentum showing solid sheets of cells. All sections were cut from the same block of tissue with location controls in the left hand column and location tests in the right hand column: DAPI (A); anti-RhoA (B); anti-GCLC (C); anti-phospho-GLUT1 (D); abti-ASCT2 (E); anti-TKTLP1 (F). DAPI identifies nuclei whereas ASCT2 identifies the locations of the plasma membranes. RhoA, phospho-GLUT1, and TKTLP1 are primarily found in a peripheral distribution, in contrast with GCLC, which is not. These findings parallel those of recurrent DCIS samples. (N=3) (Bar=50 μm) Higher magnification images of Panels A and B are shown in FIG. 4
Figure 9:
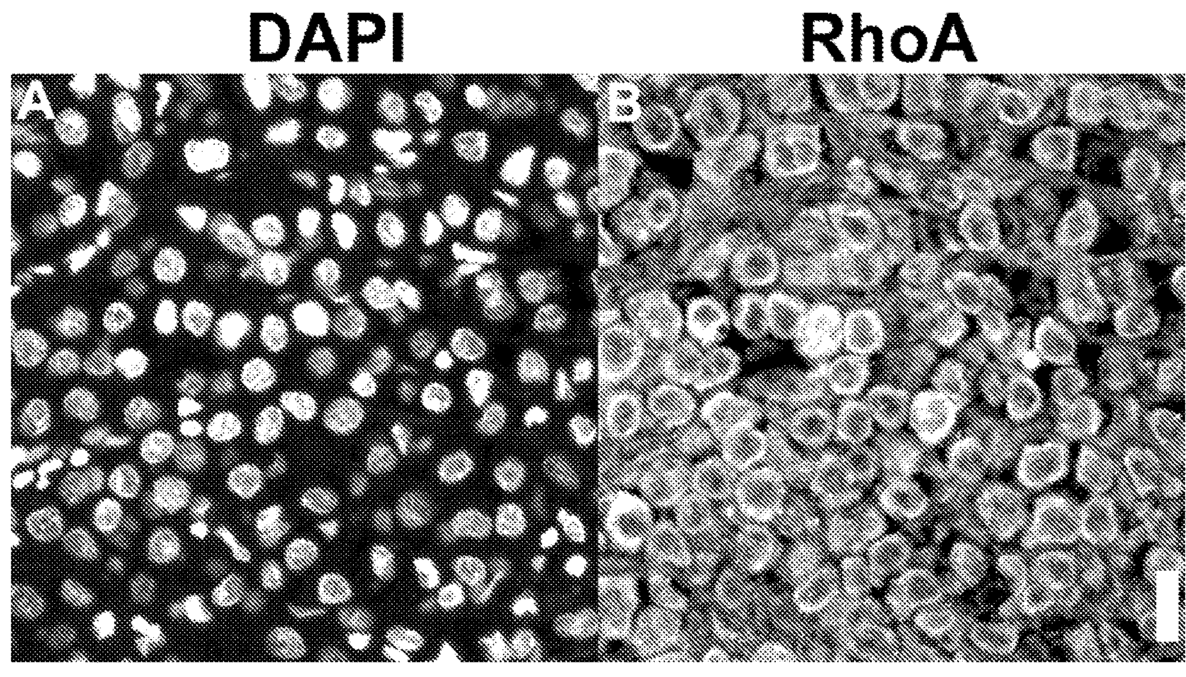
FIG. 9 is micrographs of RhoA Labeling of a Sample of Breast Cancer Metastasis to the Omentum. RhoA (B) is primarily found in a peripheral distribution, whereas DAPI (A) is found near the cell center. These finding is similar to that found in recurrent DCIS samples. (N=3) (Bar=50 μm)

The role of protein location in recurrent cancer is supported by the peripheral accumulation of not one protein, but ten proteins; five of these proteins (RhoA, RhoA(GTP), phospho-GLUT1, TKTLP1, and GS) are statistically very strongly linked to recurrent cancer. This property of DCIS tissue samples from patients who will recur is shared with metastatic breast cancer cells (FIGS. 8 and 9). However, GCLC was rarely found at the cell periphery. As the serum concentration of its product γGC, is higher (7 μM) than the cytosolic level (Ref 43; incorporated by reference in its entirety), γGC is known to enter cells, and to participate in GSH synthesis (Refs. 43-46; incorporated by reference in their entireties). Moreover, cell surface γ-glutamyl transpeptidase (GGT), in the presence of a γ-glutamyl donor such as glutamine, synthesizes γGC (FIG. 1) (Refs. 42, 43; incorporated by reference in their entireties). As GCLC is inhibited by GSH (Ref 46; incorporated by reference in its entirety), its lack of trafficking to the cell periphery may not limit GSH formation. It is contemplated that increases in GSH concentrations cause GDP release from RhoA(GDP) thus leading to RhoA(GTP) formation because of the high cytosolic levels of GTP; RhoA(GTP) then promotes recurrences.

The robust diagnostic ability of enzyme and transporter trafficking to the plasma membrane of DCIS samples prior to breast cancer recurrences provides an accurate diagnostic test to identify at risk DCIS patients. The methods herein prevent the over-diagnosis of life-threatening cancer; thereby reducing the need for unnecessary treatments.

Some embodiments herein employ machine learning to improve outcome predictions. Some embodiments employ diagnostic machine vision applications within imaging software such that outcomes are calculated/evaluated at the time of initial diagnosis.

The present disclosure provides methods of predicting cancer recurrence in a subject, methods of preventing cancer recurrence in a subject and methods for distinguishing recurrent from non-recurrent cancer. The methods comprise determining intracellular localization of at least one biomarker for cancer recurrence in a sample from a subject comprising cancer cells. The methods may further comprise predicting cancer recurrence in the subject. In some embodiments, peripheral intracellular localization of at least one biomarker predicts cancer recurrence or indicates recurrent cancer. A biomarker has peripheral intracellular localization when it is not centrally or homogeneously located throughout the cell but rather the localization is towards the edges of the cell near the cell membrane.

The intracellular localization may be determined using any histochemical analysis well known in the art. Histochemical analyses include but are not limited to, immunohistochemistry or immunostaining, cytochemistry, histopathology, in situ hybridization, and the use of molecular probes. Texts illustrating histochemical techniques include "Histochemical and Immunochemical Techniques: Application to pharmacology and toxicology," (1991) Bach, P. and Baker, J., eds., Chapman & Hall, New York, N.Y. pp 1-9, and in "Stains and Cytochemical Methods," (1993) M. A. Hayat, ed., Plenum Press, New York, N.Y., incorporated herein by reference.

In some embodiments, determining intracellular localization of at least one biomarker for cancer recurrence comprises: a) immunostaining the sample with a primary antibody directed to at least one biomarker for cancer recurrence; and b) imaging the sample.

Detecting the primary antibody may be done directly or indirectly. In some embodiments, the primary antibody is detected with a secondary antibody configured to noncovalently attached to the primary antibody. Examples of secondary antibody include anti-mouse, rabbit, bovine, goat, sheep, dog and chicken antibodies. The secondary antibody comprises a detectable label, e.g. a fluorescent tag, a luminescent tag, an enzyme, an enzyme substrate, or a radiolabel covalently attached to the antibody. In some embodiments, the primary antibody is detected by a non-antibody binding protein such as protein G, protein A, protein L, and a lectin which may contain a detectable label as described for the secondary antibody.

Alternatively, the primary antibody may contain a detectable label, as described above, or may be modified with another type of label (e.g. biotin) that binds or interacts with a labeled or non-labeled non-antibody binding partner (e.g. streptavidin).

The type of imaging will be dictated by the detectable labels employed. In exemplary embodiments, a secondary antibody is fluorescently labeled and the imaging comprises fluorescence microscopy. In some embodiments, the secondary antibody comprises an enzyme (e.g. peroxidase or alkaline phosphatase) that produces colored products detectable by light microscopy. In some embodiments, the secondary antibody comprises a radioactive label which can be visualized by autoradiography.

The method may further comprise immunostaining for organelles and other cellular structures, e.g., nuclei and cell membranes, using known methods in the art.

The biomarkers for cancer recurrence may comprise enzymes and transporters involved in the glutathione cycle including, but not limited to, glutamate cysteine ligase catalytic domain (GCLC), glutathione synthetase (GS), cystine-glutamate antiporter (xCT), CD44v9, glutamine uptake transporters ASCT2, ATBO+ and LAT1, leucine uptake (LAT1), g-glutamyl transpeptidase (GGT), g-glutamyl cysteine (gGC), glucose transporter 1 (GLUT1), glucose 6-phosphate dehydrogenase (G6PD), transketolase (TKT), transketolase-like protein 1 (TKTLP1), RhoA, RhoA with bound GTP and CD74. In some embodiments, the biomarkers for cancer recurrence are selected from the group consisting of phosphorylated glucose transporter type 1, transketolase-like protein-1, glutathione synthetase, GTP-loaded RhoA, RhoA and any combination thereof. Peripheral intracellular localization of phosphorylated glucose transporter type 1, transketolase-like protein-1, glutathione synthetase, GTP-loaded RhoA, RhoA and any combination thereof predicts cancer recurrence or indicates recurrent cancer.

The cancer may be a carcinoma, sarcoma, lymphoma, leukemia, melanoma, mesothelioma, multiple myeloma, or seminoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus. In some embodiments, the cancer is selected from breast cancer, prostate cancer, lung cancer, melanoma, kidney cancer, thyroid cancer, pancreatic cancer, stomach cancer or bladder cancer. The breast cancer may comprise ductal carcinoma in situ of the breast (DICS), lobular carcinoma in situ (LCIS), atypical ductal hyperplasia (ADH), or atypical lobular hyperplasia (ALH). In some embodiments, the cancer recurrence is ipsilateral breast cancer recurrence.

The sample may be any sample which comprises cancer cells, such as a sample from a subject, such as a cancer biopsy or other conventional pathology samples. In some embodiments, the sample comprises a formalin-fixed paraffin-embedded cancer tissue sample or a cancer metastases tissue or cell sample.

The methods may further comprise treating a subject predicted to have cancer recurrence. The treatment or therapeutic regimen may include, but is not limited to, surgery, administration of an inhibitor of enzyme accumulation at the plasma membrane immunotherapy, radiotherapy, administration of a chemotherapeutic agent. In some embodiments, the treatment or therapeutic regimen comprises surgery. In some embodiments, the treatment or therapeutic regimen comprises administration of inhibitors to enzyme or transporter accumulation at plasma membrane. Inhibitors to enzyme accumulation at plasma membrane include, but are not limited to, colchicine, taxol, calmodulin antagonists, anesthetics (e.g. local anesthetics — see Schwartz D, et al, *Mol Genet Metab.* 2000; 69(2):159-164, incorporated herein by reference in its entirety) and prenylation inhibitors. In some embodiments, the treatment regimen comprises one or more of surgery; administration of inhibitors to enzyme accumulation at plasma membrane; immunotherapy; radiotherapy; and administration of a chemotherapeutic agent.

Tumor cells exhibiting enzyme and transporter trafficking may have high GSH levels and may be able to resist oxidant-mediated chemotherapy and radiotherapy. It is contemplated that inhibition of enzyme and transporter trafficking to the cell periphery in recurrent disease may cause recurrent cancer cells to assume the metabolic properties of non-recurrent cancer cells. In some embodiments, agents inhibiting enzyme accumulation at the plasma membrane are administered to increase the radiosensitivity and chemosensitivity for redox-active drugs. Drug-mediated detachment of glycolytic enzymes from plasma membranes and cytoskeletons (e.g., colchicine, taxol, calmodulin antagonists) have been reported. In some embodiments, DCIS patients exhibiting RhoA and RhoA(GTP) trafficking benefit from prenylation inhibitors (Ref 47; incorporated by reference in its entirety), because RhoA's membrane form can undergo prenylation. Thus, in some embodiments, the treatment regimen comprises co-administration of inhibitors of enzyme and transporter accumulation at the plasma membrane and chemotherapy or radiotherapy.

In cases of co-administration or selection of more than one treatment regimen, the different therapeutic regimens may be administered together, separately, or subsequently to each other separated by a period of time. For example, the treatment with inhibitors of enzyme and transporter accumulation at plasma membrane may precede any chemotherapy and radiotherapy by a period of time ranging from 1 day to 60 days or surgery may precede administration of inhibitors to enzyme accumulation at plasma membrane, immunotherapy, radiotherapy, or administration of a chemotherapeutic agent.

In those instances when the subject is not predicted to have recurrent cancer, the subject may be monitored and subsequent analysis may be completed during the course of monitoring.

The present disclosure also provides systems (e.g., reagents, computer software, imaging instruments, etc.) for predicting cancer recurrence or distinguishing between recurrent and non-recurrent cancer. The systems may comprise at least one or all of a sample (e.g., positive and/or negative control samples), a primary antibody to a biomarker for cancer recurrence, an imaging instrument (e.g. fluorescence or brightfield microscope), and software configured to determine the intracellular location of the biomarker for cancer recurrence. The description of a sample, biomarkers for cancer recurrence and imaging techniques described elsewhere herein are also applicable to the disclosed system.

The software may be supplied with the systems in any electronic form such as a computer readable device, an internet download, or a web-based portal. The software may be integrated with the imaging instrument to not only determine the intracellular location of the biomarker for cancer recurrence but also predict cancer recurrence. The software may allow a user to view results in real-time, review results of previous samples, and view reports.

The systems can also comprise instructions for using the components of the systems. The instructions are relevant materials or methodologies pertaining to the systems. The materials may include any combination of the following: background information, list of components and their availability information (purchase information, etc.), brief or detailed protocols for using the systems, trouble-shooting, references, technical support, and any other related documents. Instructions can be supplied with the systems or as a separate member component, either as a paper form or an electronic form which may be supplied on computer readable memory device or downloaded from an internet website, or as recorded presentation.

It is understood that the disclosed systems can be employed in connection with the disclosed methods.

EXAMPLES

Materials and Methods

Study design A retrospective discovery study was conducted of DCIS lesions from surgical biopsies to develop a diagnostic test. The objective was to quantitatively compare intracellular patterns of enzymes and transporters within archival FFPE tissue samples of patients experiencing cancer recurrences to those not reporting recurrences. Digital fluorescence images were read by computer using machine learning software. The primary reference standard ("gold" standard) was patient outcome. This gold standard was limited by potential and known false positives and false negatives. Computer predictions were used as a second reference standard. The endpoint was achieved when the precision and recall were ≥90%.

DCIS patient samples Pure DCIS samples from 70 women (50 non-recurrent, 20 recurrent) who were followed for at least 10 years were used. As non-recurrent samples were more heterogeneous than recurrent samples (e.g., labels were found at centrioles, the vicinity of the cell center, and uniformly distributed within cells of non-recurrent samples) their analysis required a larger number of samples. For all DCIS samples, no evidence of lymph node involvement was noted. No evidence of invasive cancer was present. For samples from recurrent patients, the mean disease-free period before recurrence was 90 ±80 months. Samples were from partial or total mastectomies of patients aged 37-80 years after informed consent was obtained. Patients had no previous or concurrent cancer. Formalin-fixed paraffin-embedded (FFPE) pathology samples were obtained from the St. Louis Breast Tissue Registry (St. Louis, MO). This blinded tissue sourcing strategy was used to ensure that laboratory personnel did not have access to electronic medical records of patients whose samples were under study. No patient samples were excluded from the data analysis procedures.

Metastatic breast cancer samples To permit a comparison with recurrent DCIS samples, tissue samples of breast cancer metastases were examined. Samples of breast cancer metastases were obtained from the NDRI (National Disease Research Interchange; Philadelphia, PA). Breast cancer metastases were confirmed by the finding that the sample was estrogen receptor positive, cytokeratin 7 positive, and cytokeratin 20 negative on the basis of immunohistochemistry. The use of human material was in accordance with the Declaration of Helsinki on the use of material in scientific research. All experiments were approved by the University of Michigan IRB.

Immunofluorescence of tissue sections FFPE samples were cut into 5 μm thick sections. Sections were de-paraffinized and re-hydrated by sequential incubation in a graded ethanol series. After rehydration in PBS with 0.02% Triton X-100 (Thermo-Fisher Sci.), sections were subjected to heat-mediated antigen retrieval in 10 mM citric acid buffer, pH 6.0. Sections were blocked using a blocking solution (10% dried milk in PBS) for 1 hr. at room temperature. After blocking procedures, sections were incubated with 2 μg/mL of antibody (Tables 1 and 2) diluted in 1% BSA in PBS overnight at 4° C. After incubation, the sections were washed with PBS. Finally, the sections were incubated with fluorescently-labeled secondary antibody for 1 hr., washed with PBS, and then mounted in Prolong Diamond Antifade medium.

TABLE 1

Primary Antibodies

| Target | Species | Provider | Cat. No. | Concentration | μg/mL |
|---|---|---|---|---|---|
| CD44 | Rabbit | abcam | ab51037 | 1.072 mg/mL | 1.86 |
| CD24 | Mouse | Biolegend | 311102 | 0.5 mg/mL | 4 |
| RhoA | Rabbit | abcam | ab236278(Lot GR324123 6-1) | 4.5 mg/mL | 0.44 |
| RhoA | Rabbit | abcam | ab236278 (Lot GR324123 6-2) | 1 mg/mL | 2 |
| RhoA-GTP | Mouse | NewEast Bioscience | 26904 | 1 mg/ml | 2 |
| CD44v9 | Rat | NewEast Bioscience | 394402 | 0.5 mg/mL | 4 |
| CD24 | Rabbit | abcam | ab199146 | 1.8 mg/mL | 1.1 |
| Transketolase | Mouse | abcam | Ab772997 | 1 mg/mL | 2 |
| TKTL1 | Rabbit | abcam | Ab155662 | 0.95 mg/mL | 2.1 |
| xCT | Rabbit | abcam | Ab37185 | 1 mg/mL | 2 |
| SLC7A5/LAT1 | Rabbit | abcam | Ab18493 | 0.79 mg/mL | 2.5 |
| ASCT2 | Rabbit | abcam | Ab237704 | 0.5 mg/mL | 4 |
| ABT0+ (SLC6A14) | Rabbit | Sigma | HPA00319 | 0.1 mg/mL | 20 |
| G6PD | Mouse | Santa Cruz | Sc-373886 | 200 μg/mL | 10 |
| GCLC | Mouse | Invitrogen | MA5-26346 | 1 mg/mL | 2 |
| Phospho-GLUT1 | Rabbit | Sigma | ABN991 | 1 mg/mL | 2 |
| GLUT1 | Mouse | abcam | Ab40084 | Unknown | 1/150 |
| CD74 | Mouse | abcam | Ab9514 | Unknown | 1/100 |
| Glut1 | Rabbit | abcam | Ab652 | 1 ?L/500 μL | 2 |
| GS | Mouse | Novus | NBP2-03351 | Unknown | 6.6 |
| GGT | Mouse | abcam | Ab55138 | 1 mg/mL | 2 |

TABLE 2

Secondary Antibodies

| Target | Species | Type | Concentration | μg/mL |
|---|---|---|---|---|
| Rabbit | Donkey | AlexaFluor568 | 2 mg/mL | 10 |
| Mouse | Goat | AlexaFluor488 | 2 mg/mL | 10 |
| Rat | Goat | AlexaFluor488 | 2 mg/mL | 10 |
| Sheep | Donkey | AlexaFluor568 | 2 mg/mL | 10 |

DAPI staining To assess protein location in breast cancer metastases, cell nuclei were labeled with DAPI. After antigen retrieval, slides were washed then incubated with DAPI for 30 min. at a concentration of 300 nM (Fisher, Waltham, MA) (48). Samples were then mounted in Prolong Diamond Antifade mounting medium (Thermo-Fisher Sci.).

Imaging Fluorescence microscopy was performed (Refs. 49, 50; incorporated by reference in their entireties) using a Nikon TE2000-U inverted microscope (Nikon, Melville, NY) and a back-illuminated Andor iXon electron-multiplying charge-coupled device (EMCCD) camera (Model DV-887; Andor Technology, Belfast, Northern Ireland). To confirm that the findings are independent of the detector, experiments were also performed with an Andor Model DU-888 back-illuminated EMCCD camera. Due to the optical set-up, a 1.5× optivar was used to create the same level of magnification at the detector. Results were independent of the detector for these cameras. Images were captured and processed with Metamorph software (Molecular Devices, Downingtown, PA). To reduce shot noise, each micrograph was an average of 10-15 images, with each image acquired for 0.2 sec. To reduce read noise, the EMCCD chip was cooled to −95° C. Typical camera settings were: multiplication gain, 100; vertical shift speed, 3.04 msec./pixel and 14-bit digitization at 10 MHz. Micrographs were evaluated using ImageJ software. Images were evaluated and auto-scaled by using ImageJ.

Statistical analysis of categorical data The statistical significance of comparisons of biomarker locations in samples from patients experiencing a cancer recurrence and recurrence-free patients was assessed using contingency tables. Two-by-two contingency tables were constructed using the categorical variables of peripheral or non-peripheral staining. Tests were performed with the “N-1” chi-squared procedure as implemented by Campbell (Ref 51; incorporated by reference in its entirety).

Figure 10A:
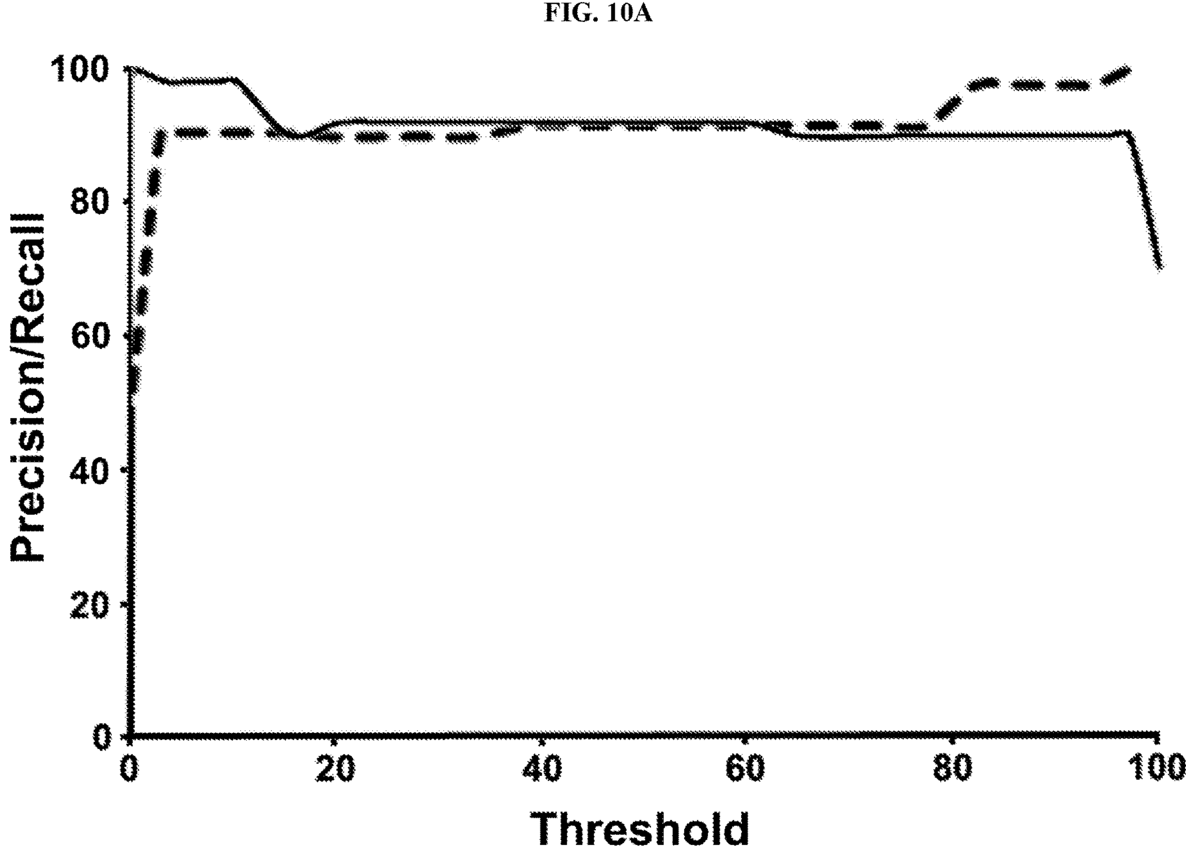
FIGS. 10A and 10B are graphs of precision-recall curves for machine-based recognition of recurrent and non-recurrent cancer. The precision (solid) and recall (dashed) are plotted separately as a function of threshold.

Computational outcome prediction Outcome prediction was performed using machine learning. The Custom Vision application of Microsoft’s (Redmond, WA) Azure Cognitive Services platform was used. Custom Vision is a state-of-the-art computer vision application. This software tool was deployed as a multiclass (tags: recurrent or non-recurrent) and general domain problem. The computer was trained with micrographs of phospho-GLUT1. Machine training was based on tissues exhibiting peripheral or non-peripheral labeling patterns. This approach minimized the introduction of confounding errors by excluding known false negatives (contralateral recurrences) and apparent false positives (recurrence-free patients with peripheral trafficking of protein markers) from the computer model. Limited dataset size is a common problem in medical machine vision applications. To deflect this issue, image augmentation was used (Ref 52; incorporated by reference in its entirety). Image mirroring was used to increase the dataset’s size. The performance of the computer model was assessed by calculating precision and recall. The precision (or positive predictive value)=TP/(TP+FP) where TP=true positives and FP=false positives. The recall is defined as TP/(TP+FN) where FN=false negatives. Data were evaluated using precision-recall curves, which plot these variables across many threshold values. Precision-recall curves are much less sensitive to differences in the numbers of patients in each group than receiver operating characteristic plots (Ref 53; incorporated by reference in its entirety). The resulting model was a robust predictor of patient outcomes (Table 3; FIG. 10). The cut-point was typically used at a threshold of 50%, as illustrated in FIG. 10. The probability of outcome for each micrograph undergoing computer-assisted diagnosis as recurrent or non-recurrent was generally 99.9 or 100%.

Example 1

Localization of RhoA at the Plasma Membrane in DCIS

Figure 2:
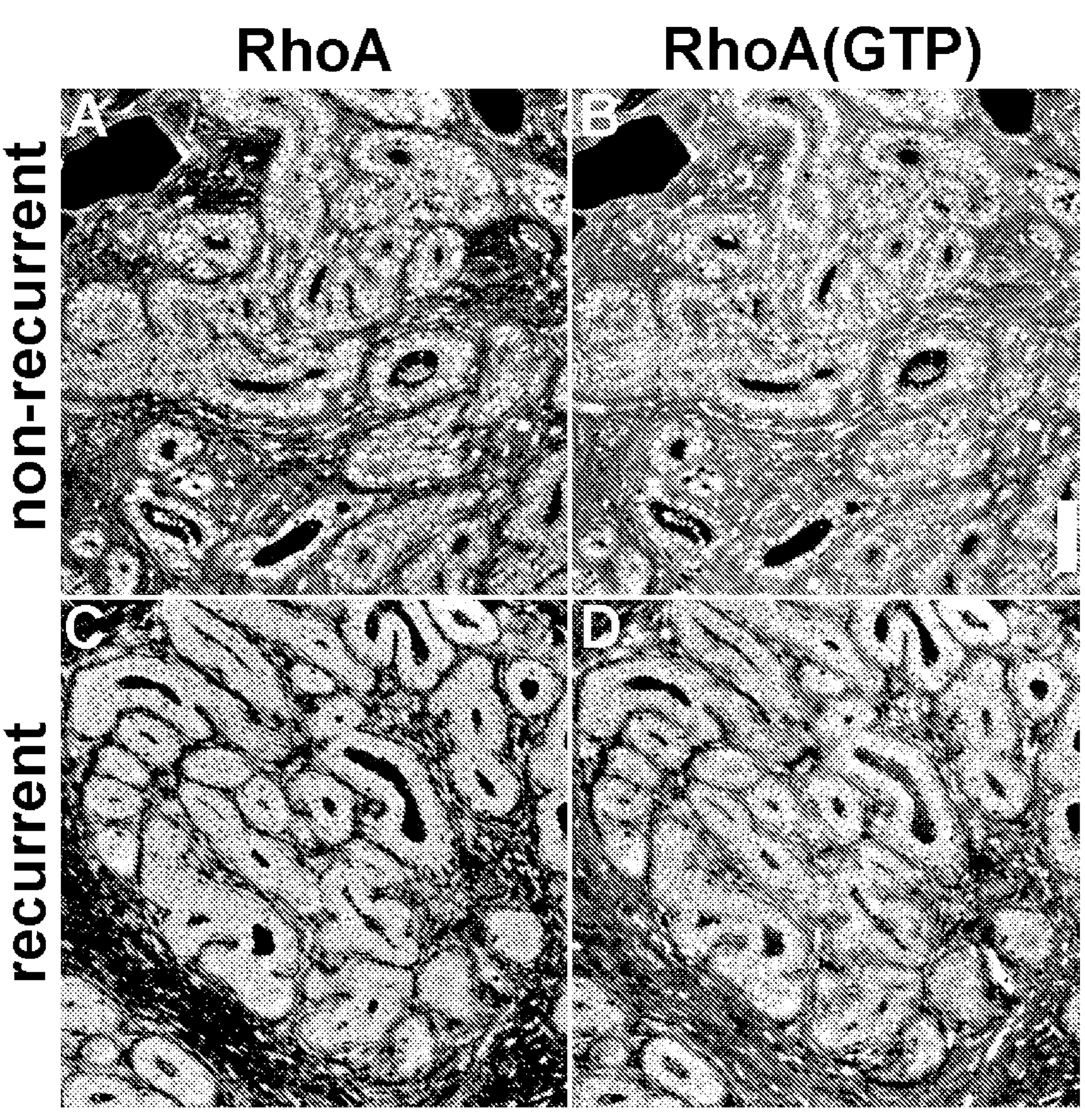
FIG. 2 is micrographs of tissue sections from surgical biopsies of DCIS patients subsequently found to exhibit nonrecurrent (A, B) or recurrent (C, D) cancer. Both RhoA (A, C) and RhoA(GTP) (B, D) were found in a central distribution within epithelial cells of patients who did not experience a recurrence. In contrast, RhoA and RhoA(GTP) adopt a peripheral pattern in epithelial cells of patients who later experience a recurrence. Of course, other cell types within the sections, such as mesenchymal cells, may also be stained with anti-RhoA reagents. (Bar=50 μm)

RhoA localization was investigated in ductal epithelial cells of archival DCIS samples from patients who did or did not experience a breast cancer recurrence. As RhoA molecules are linked to invasive cancer and translocate to plasma membranes in other diseases (Refs. 20, 21, 37; incorporated by reference in their entireties), its localization was studied as a potential prognostic test for cancer recurrences. DCIS sections were stained with an antibody directed against an activation-specific epitope of RhoA (GTP) and a second antibody that binds to RhoA molecules (RhoA). FIG. 2A, B shows dual wavelength fluorescence micrographs of a tissue section from a non-recurrent DCIS patient labeled with RhoA and RhoA(GTP) reagents. Neither RhoA nor RhoA(GTP) is found at the cell periphery. However, both RhoA and RhoA(GTP) are found at the epithelial cell periphery in DCIS tissue samples from patients with recurrent disease (FIG. 2C, D). RhoA’s location was treated as a categorical variable (peripheral or not peripheral) to permit statistical analyses. The two-by-two contingency table was analyzed by the “N-1” chi-squared test, which showed $P<0.001$. Similarly, RhoA(GTP) locations within epithelial cells of tissue samples from women with recurrent and non-recurrent cancer exhibited $P=0.001$. RhoA and RhoA(GTP) accumulation near the plasma membrane’s vicinity is a cellular feature of recurrent cancer, but not non-recurrent disease.

Example 2

Localization of GLUT1 and PPP Enzymes in DCIS

Figure 3:
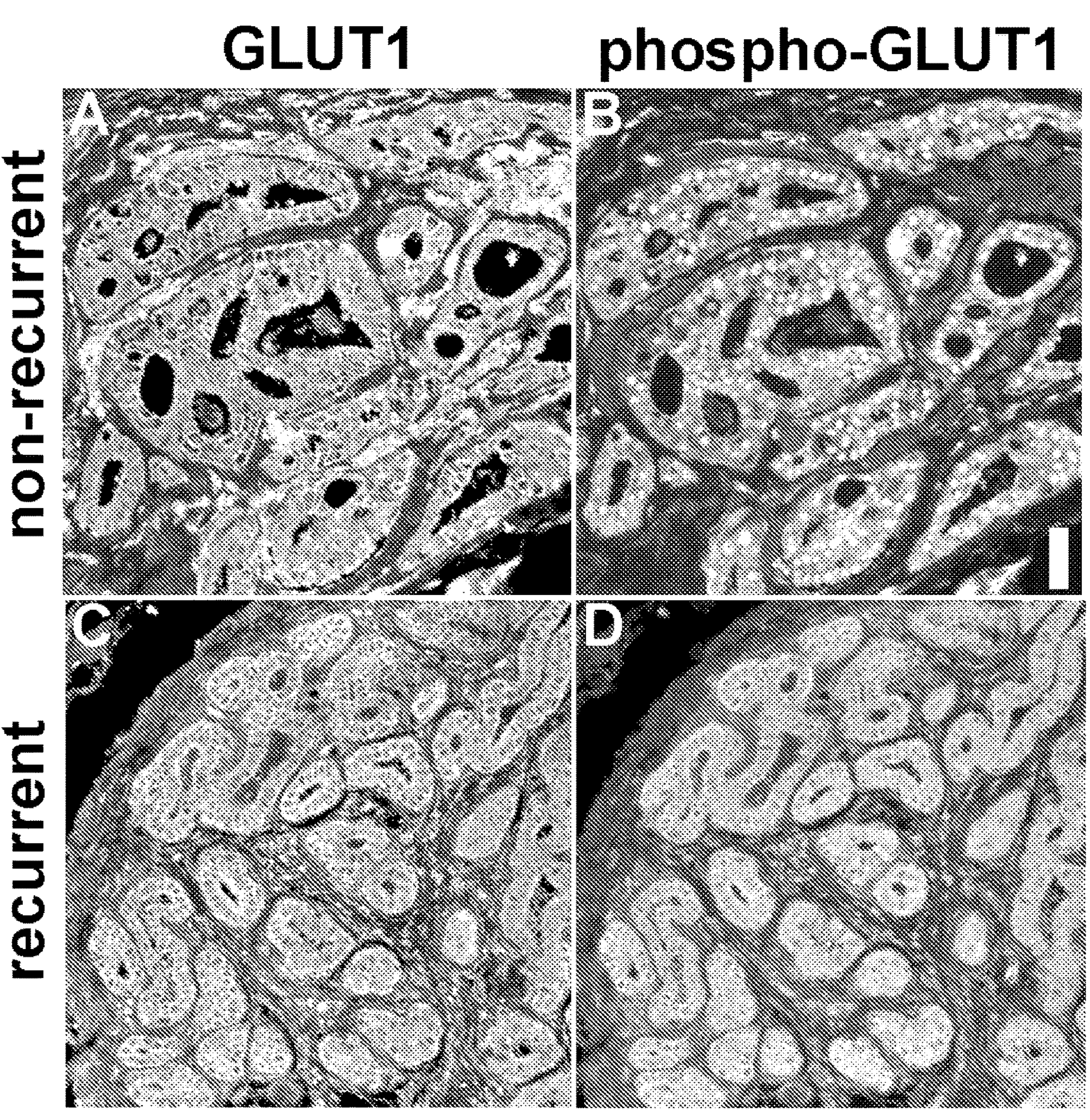
FIG. 3 is micrographs of GLUT1 and phospho-GLUT1 within cells of biopsies from DCIS patients subsequently found to exhibit non-recurrent (A, B) or recurrent (C, D) cancer. Tissue samples from patients with non-recurrent disease demonstrated a peripheral distribution of GLUT1 within epithelial cells (A), but the phosphorylated form a GLUT1 (B) was found in a central location. For patients experiencing a recurrence, GLUT1 and phospho-GLUT1 are found at the epithelial cell periphery (C, D). (Bar=50 μm)
Figure 13:
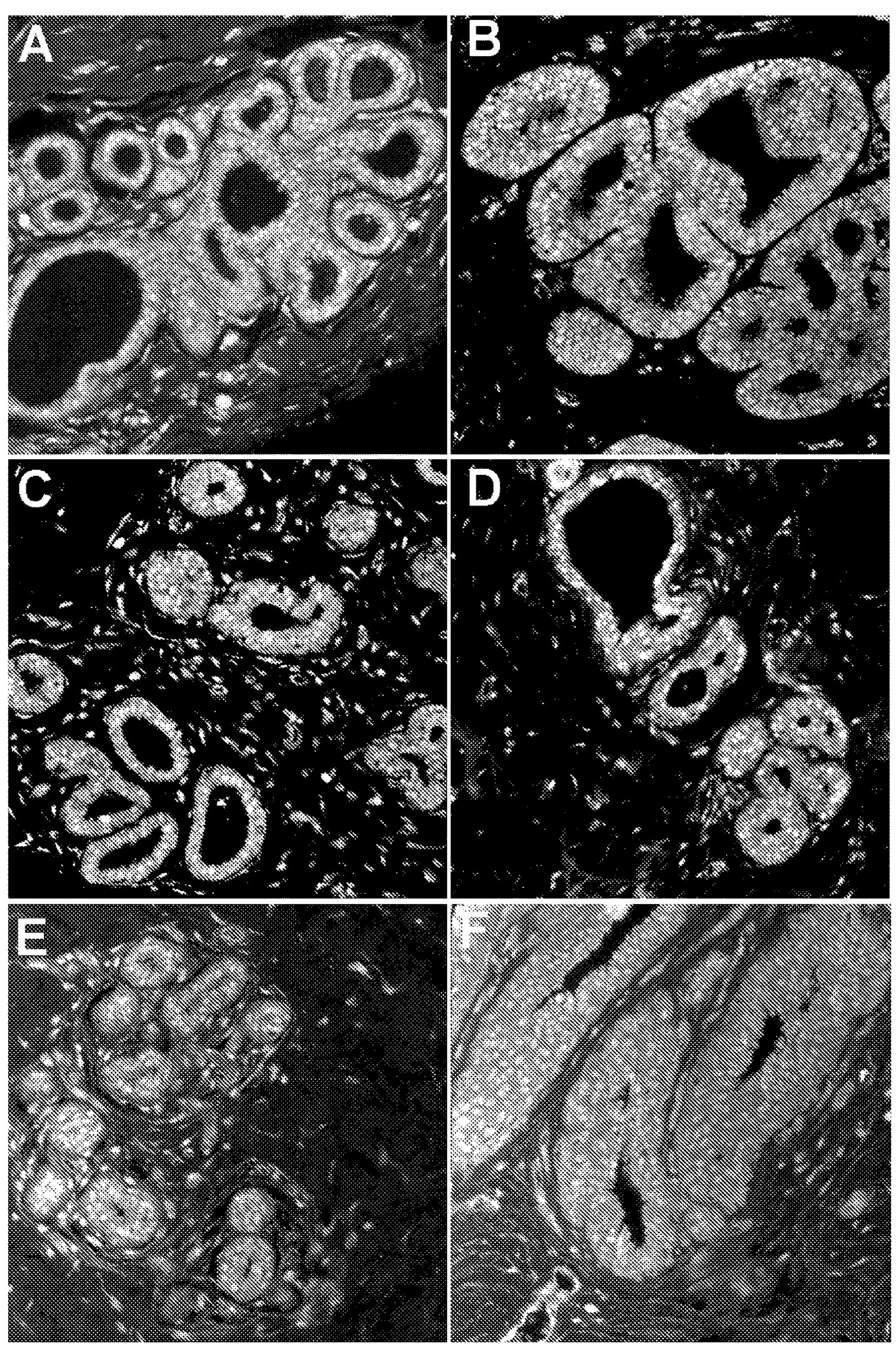
FIGS. 13A-F are micrographs of phospho-GLUT1 intracellular staining patterns of tissue samples from DCIS tissue sections from patients found to exhibit non-recurrent cancer. These images are from tissue blocks of different patients and do not include the patient samples of FIG. 3. (Bar=50 μm)
Figure 14:
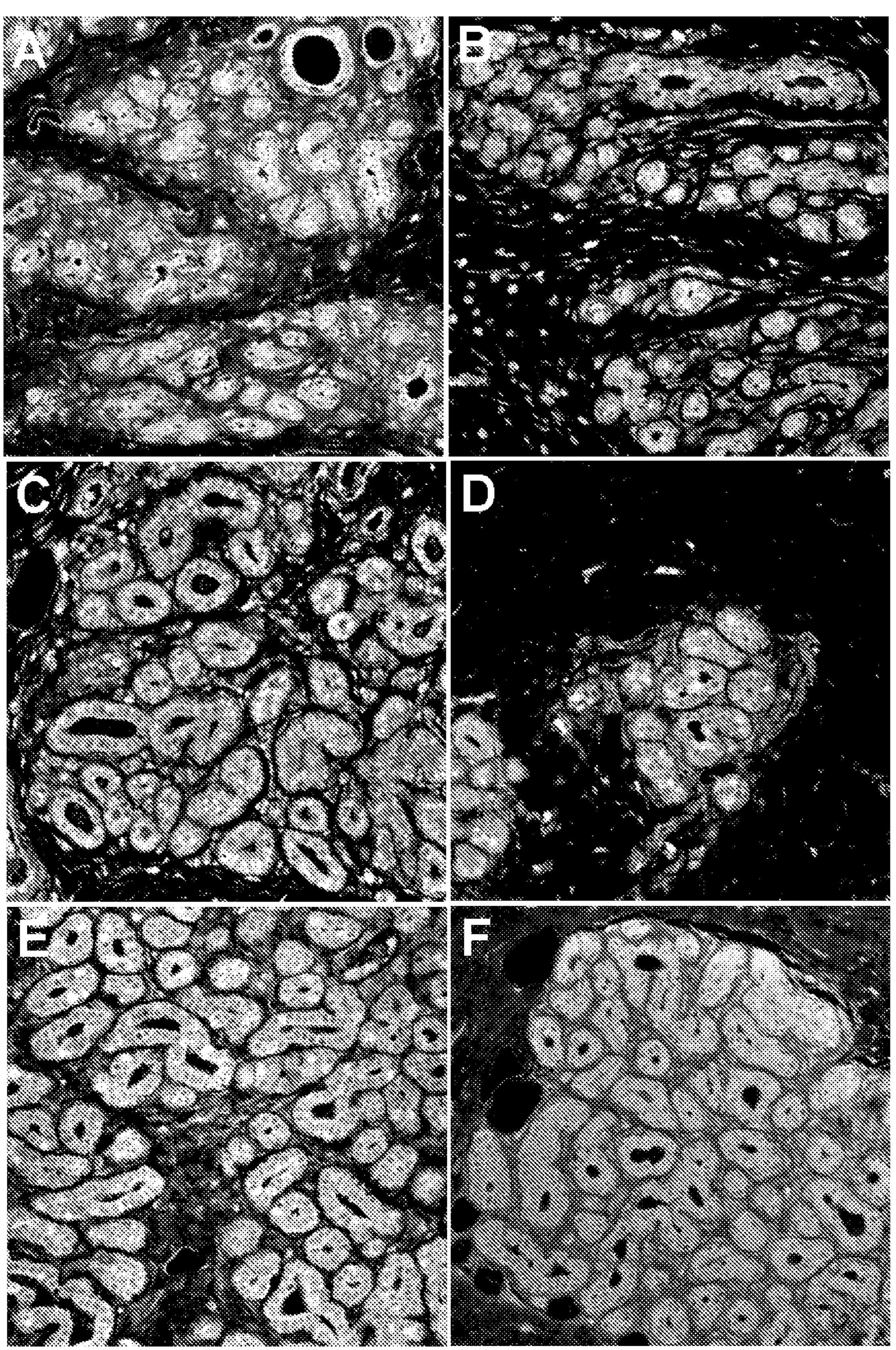
FIGS. 14A-F are micrographs of phospho-GLUT1 intracellular staining patterns of tissue samples from DCIS tissue sections from patients found to exhibit ipsilateral cancer recurrence. These images are from tissue blocks of different patients and do not include the patient samples of FIG. 3. (Bar=50 μm)

As GLUT1 is linked to breast cancer (Ref 18, 19; incorporated by reference in their entireties), its ability to distinguish between recurrent and non-recurrent patient samples was assessed. GLUT1 activity is increased by trafficking to the cell surface and phosphorylation (phospho-GLUT1) at serine-226 (Ref 38; incorporated by reference in its entirety). FIG. 3 shows fluorescence micrographs of DCIS samples stained with antibodies directed against GLUT1 and phospho-GLUT1. In samples from non-recurrent patients, GLUT1 was found at the cell periphery whereas phospho-GLUT1 was observed in a central region of cells (FIG. 3A, B). For patients experiencing recurrences, GLUT1 and phospho-GLUT1 are both found at the epithelial cell periphery (FIG. 3C, D). Additional examples of phospho-GLUT1 staining patterns of DCIS tissue sections of patients who will not experience recurrent disease and will experience a cancer recurrence are shown in FIGS. 13 and 14, respectively. Thus, anti-phospho-GLUT1 labeling of the cell periphery is correlated with cancer recurrences ($P=0.007$) and serves as a prognostic biomarker.

Next, the trafficking of the PPP enzymes, G6PD and TKTLP1, was examined in DCIS patient samples. As illustrated in FIG. 4A, B, G6PD was often found at the cell periphery in both non-recurrent and recurrent cancer ($P=0.2$). In non-recurrent DCIS, the peripheral accumulation of G6PD likely enhances ribose formation to support cell proliferation. To assess the PPP’s non-oxidative arm, TKT and TKTLP1 were examined. The micrographs of FIG. 4C-F show TKT and TKTLP1 in tissue sections of patients with and without recurrences. TKT was observed in both central and peripheral distributions whereas TKTLP1 was often observed in a peripheral distribution. In comparing non-recurrent to recurrent cancer populations, the accumulation of G6PD at the cell periphery was not significantly enhanced during recurrences whereas TKTLP1 trafficking to the periphery was significantly enhanced during recurrences ($P=0.0002$).

Example 3

Localization of GSH Synthesis Machinery and CD74 in DCIS

Figure 5:
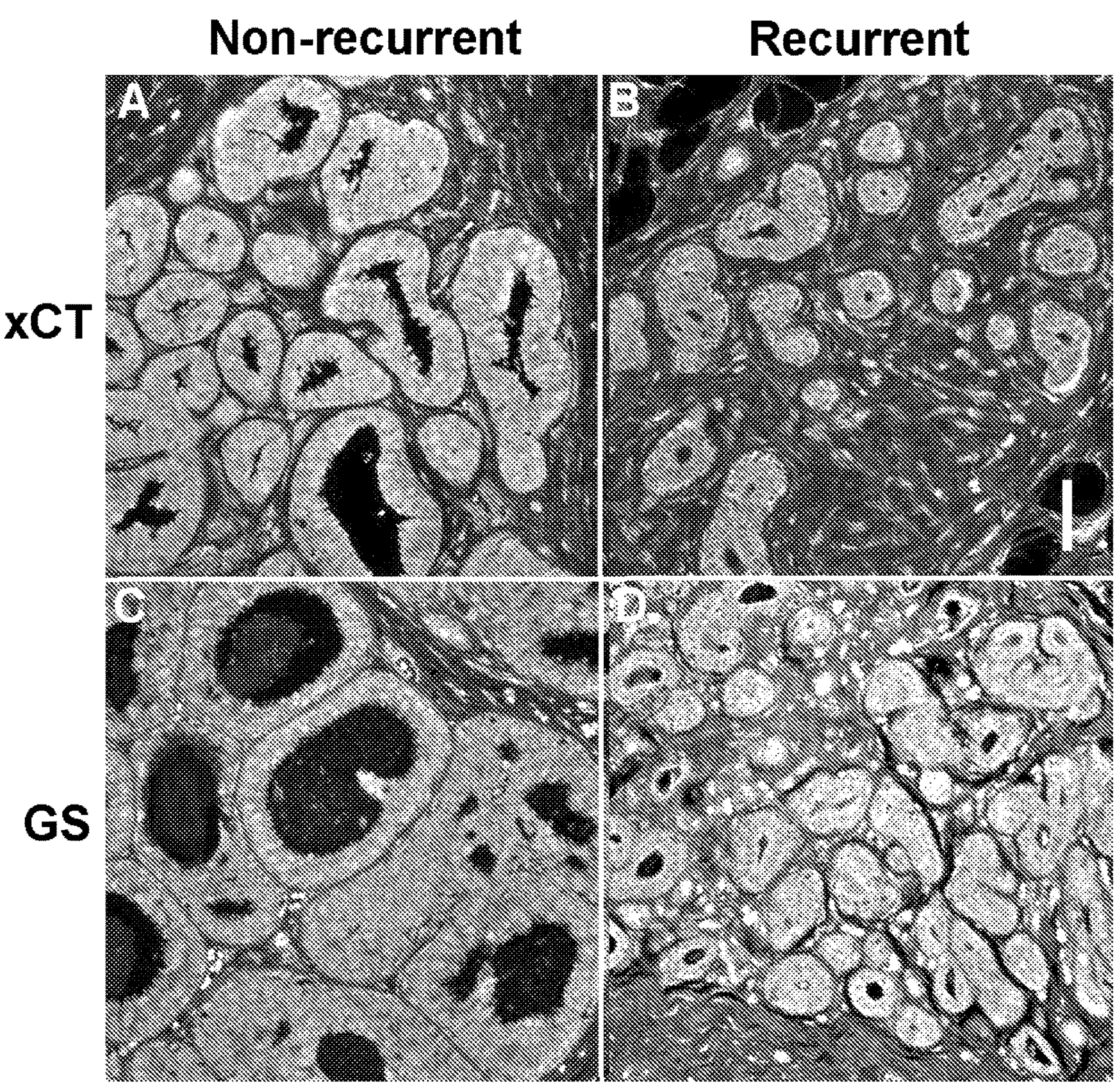
FIG. 5 is micrographs of xCT and GS in samples from non-recurrent (A, C) and recurrent (B, D) patients. xCT (A, B) and GS (C, D) can accumulate at the periphery of epithelial cells in samples from patients experiencing recurrences. (Bar=50 μm)
Figure 6:
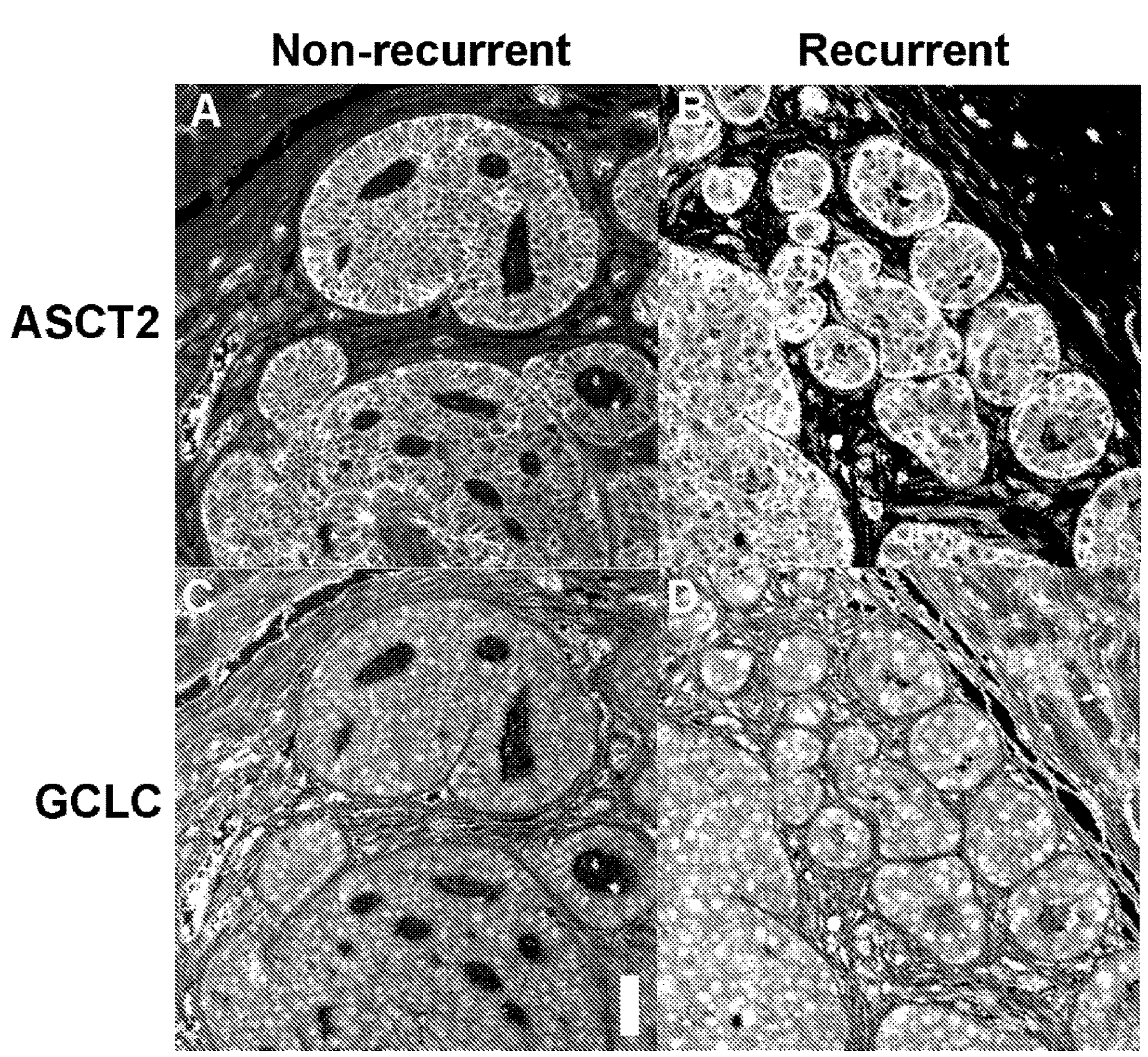
FIG. 6 is micrographs of ASCT2 and GCLC within breast tissue from patients with nonrecurrent (A, C) or recurrent (B, D) cancer. ASCT2 (A, B) was found in a peripheral pattern for tissue samples from patients with non-recurrent and recurrent disease. GCLC (C, D) was predominantly found in a non-peripheral distribution in samples from patients with non-recurrent and recurrent cancer. A substantial amount of GCLC can be found outside the ducts. (Bar=50 μm)
Figure 7:
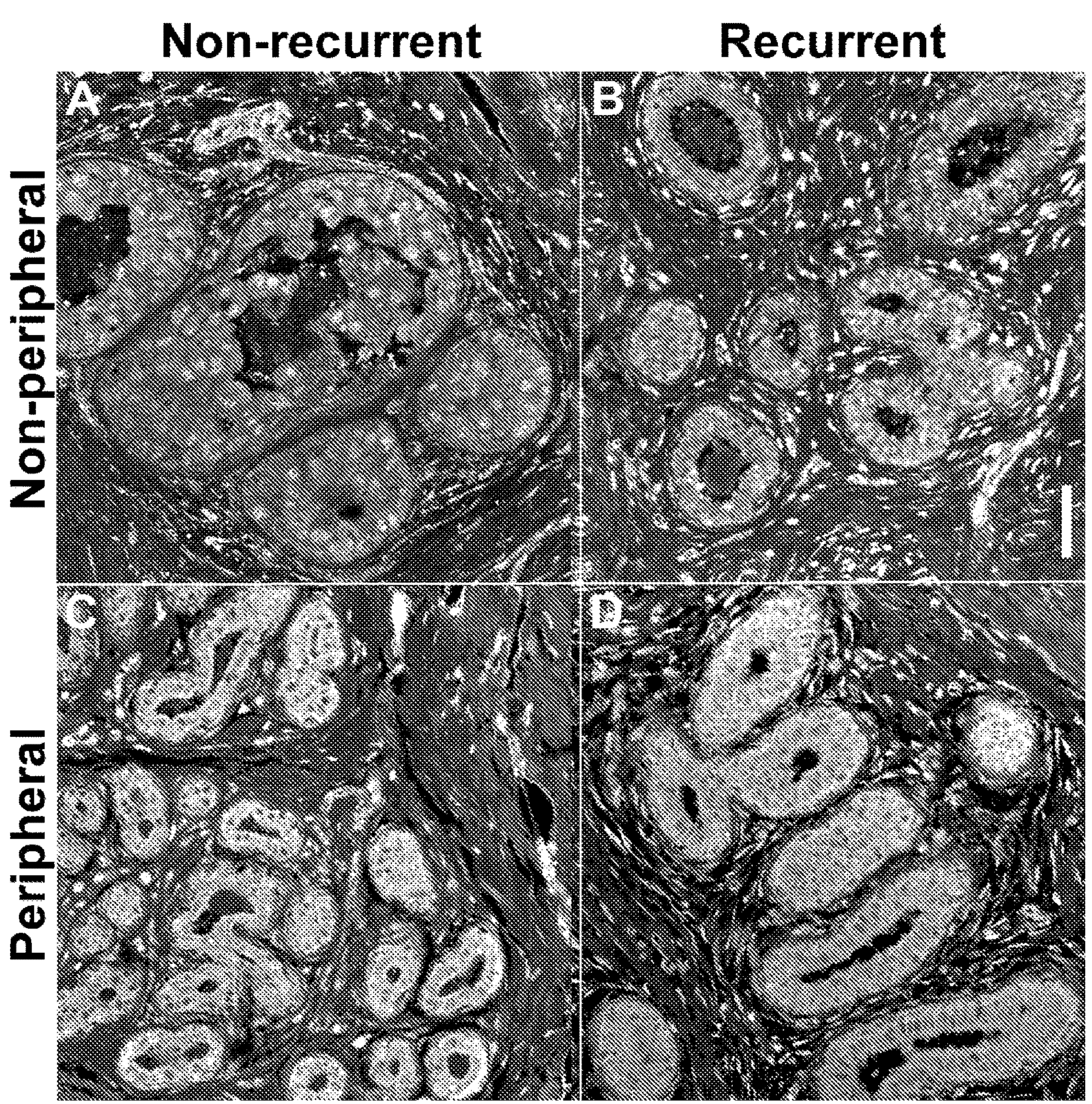
FIG. 7 is micrographs of CD44v9 in DCIS samples from non-recurrent (A, C) or recurrent (B, D) cancer. CD44v9 was found in both a central (A, B) and peripheral (C, D) distribution for both non-recurrent and recurrent disease. (Bar=50 μm)

The localization of additional relevant biomarkers was assessed. The amino acid transporters ATB0+ and ASCT2 were always found at the epithelial cell periphery for both recurrent and non-recurrent DCIS (FIG. 6A, B). GCLC, a component of the glutathione synthesis pathway, was generally not found at the cell periphery for either class of DCIS patients (FIG. 6C, D). Although CD44v9 stabilizes xCT and enhances transporter activity (Ref 9; incorporated by reference in its entirety), it could be found in peripheral and non-peripheral patterns in lesions of both non-recurrent and recurrent patient populations (FIG. 7). The transporters xCT (FIG. 5A, B) and LAT1 were more often found at the cell periphery in DCIS patient samples linked with recurrences, but not for samples of non-recurrent patients; however, they were not statistically significant (P=0.14 and P=0.06, respectively). Similarly, CD74, which is associated with poor prognoses, may be found at the cell surface in recurrent disease, but demonstrated a P value of 0.14. However, GS accumulation at the epithelial cell periphery in recurrent vs. non-recurrent patient populations demonstrated a significant P value of 0.02 (FIG. 5C, D).

Example 4

Enzyme and Transporter Localization in Metastatic Cells

Figure 4:
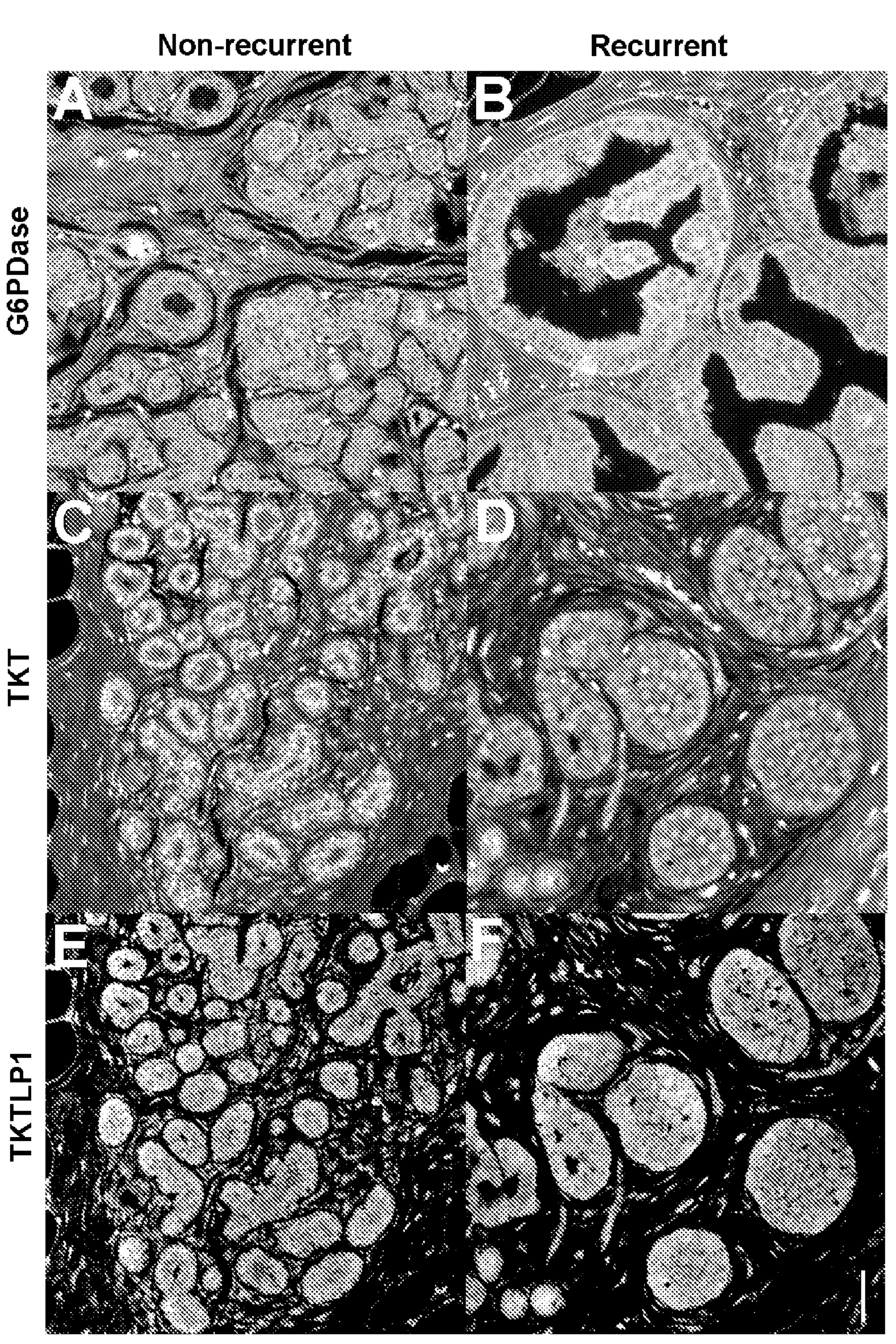
FIG. 4 is micrographs of the intracellular patterns of G6PD, TKT, and TKTLP1 in non-recurrent (A,C,E) or recurrent (B,D,F) cancer. The intracellular distributions of G6PD, TKT, and TKTLP1 were more variable than RhoA and phospho-GLUT1 in their cellular properties. G6PD and TKTLP1 tend to be peripherally located in cells whereas TKT tends to be found in a central location. (Bar=50 μm)

Experiments conducted during development of embodiments herein show that DCIS lesions exhibiting certain enzyme and transporter distribution patterns predict clinical outcomes. It was reasoned that because enzyme and transporter accumulation at the cell periphery increases GSH levels, then these proteins should also be peripherally located within metastatic cells because metastatic cells have high GSH concentrations and GSH/GSSG ratios (Ref 5). Therefore, cellular labeling patterns were analyzed in samples of breast cancer metastases. Breast cancer metastases to the omentum were used because enzyme and transporter translocation was easily observed. As FIGS. 8B and 9B show, RhoA traffics to the cell periphery whereas DAPI is found at the cell center. Thus, RhoA trafficking in metastatic breast cancer cells parallels that of ductal epithelial cells of DCIS patients destined to experience recurrences. Furthermore, peripheral trafficking was also observed for phospho-GLUT1 and TKTLP1, but not GCLC, which also agrees with our results for tissue samples from DCIS patients who will experience recurrences (FIGS. 3, 4, and 6). Thus, the enzyme and transporter trafficking events observed in recurrent DCIS samples are retained in breast cancer metastases to distant sites.

Example 5

Diagnostic Ability

The ability of biomarker labeling patterns to predict patient outcomes was assessed. As cells are smaller at the high packing densities of solid DCIS samples, intracellular trafficking is difficult to ascertain. Moreover, the forces experienced by cells at high packing densities may activate RhoA (Refs. 39, 40; incorporated by reference in their entireties), thus obscuring oncogenic signaling. Therefore, non-solid DCIS types (e.g., cribriform, papillary, micropapillary, comedo) were focused upon. It is possible to detect recurrences and non-recurrences in solid DCIS by resampling slides and blocks for non-solid regions, which were performed in these studies. Using machine learning, a computational model representing ground truth was created to predict patient outcomes. Biomarker trafficking was employed as a "gold standard" to remove false positives and false negatives from the training dataset (peripheral=recurrence and not peripheral=no recurrence). This approach is also supported by the peripheral trafficking of RhoA, phospho-GLUT1, and TKTLP1 in metastatic breast cancer (FIGS. 8 and 9). The computer was trained using images of phospho-GLUT1-tagged tissues. The test showed a precision of 94% and a recall of 94% in cross-validation testing (Table 3, FIG. 10).

TABLE 3

Performance of Computer Model using phospho-GLUT1 Labeling[1-3]

| Outcome | Precision | Recall | Avg. Performance | N |
|---|---|---|---|---|
| Non-recurrent cancer | 97.1% | 94.3% | 99.0% | 174 |
| Recurrent cancer[4] | 87.5% | 93.3% | 92.2% | 72 |

[1]Experiments utilized a 512 × 512 EMCCD chip (Andor camera model DV-887).

[2]The terms precision and recall are related parameters for classification models in machine learning.

[3]N is the number of micrographs.

[4]The recurrent cases included two patients experiencing contralateral recurrences, which reduced the performance of the test.

Using the tested computer model, based upon peripheral and non-peripheral labeling patterns, holdout validation tests were performed. A holdout validation dataset of 118 micrographs, which were not used for training, were examined. Using the reported outcomes as a gold standard the computed outcomes were found to be 80% correct, 9% false positives, and 11% false negatives, as judged by phospho-GLUT1 trafficking. However, the reported patient outcomes have known flaws regarding the underlying disease. As outcomes in the absence of surgery are unknowable ("recurrent" patients who became "non-recurrent" after surgery), false positives are expected among the patient outcomes. It was found that the tested computer model predicts ipsilateral recurrences, but cannot predict contralateral recurrences, which causes false negatives. Sampling error likely contributes to false negatives. The computer model is correct for most or all recurrences and non-recurrences in the ipsilateral breast. Machine vision was superior to human performance by ~5-12%. Diagnostic ability of protein trafficking was also noted for RhoA, RhoA(GTP), GS and TKTLP1, but not GGT or ASCT2.

Figure 10B:
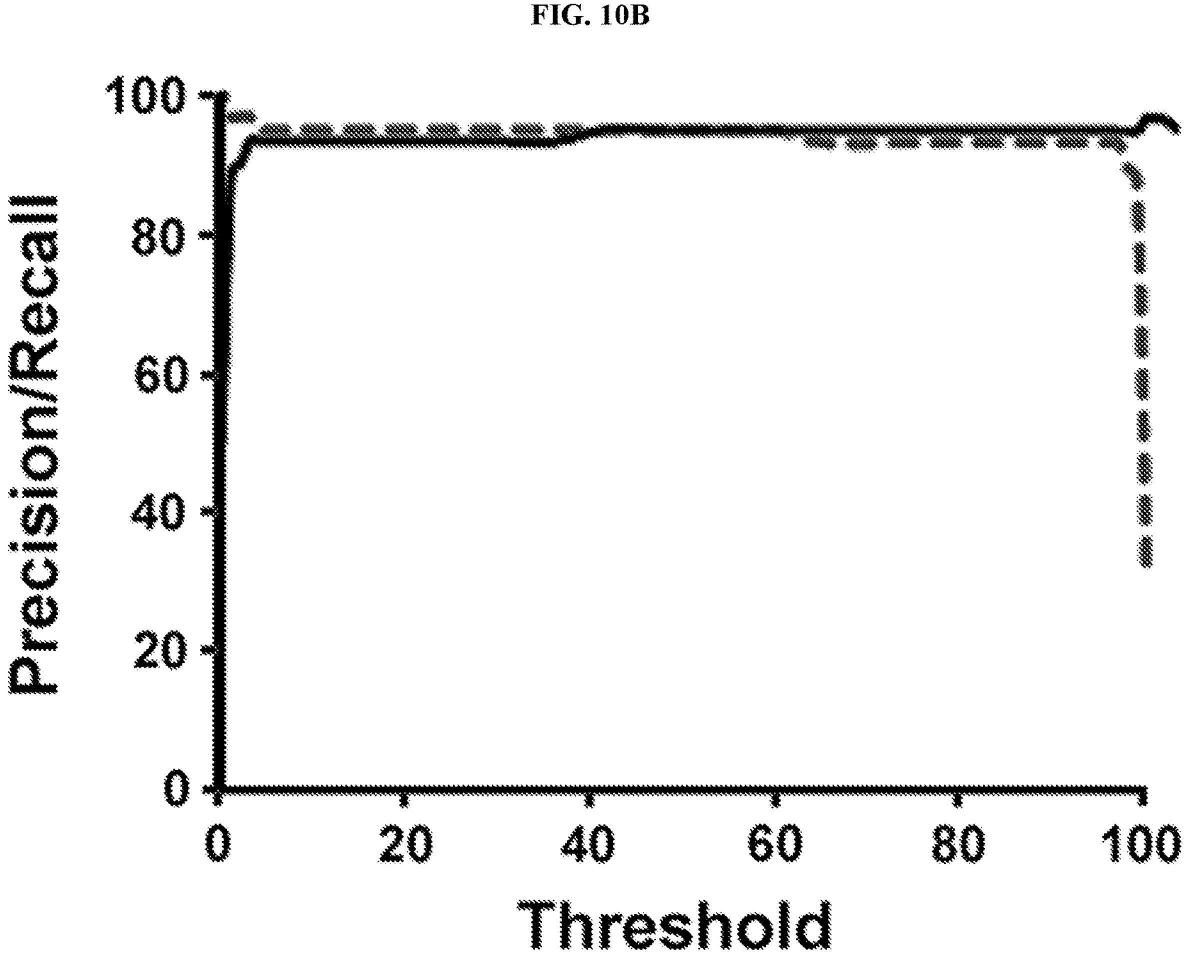

One micrograph of each patient exhibiting the highest probability of leading to recurrent cancer in the prior analysis was omitted from the training dataset used to predict patient outcomes. A threshold (a computed probability of outcome) of 50% was used. Any tissue sample exceeding this threshold in one micrograph was sufficient to classify the patient's outcome. The results of the preceding analysis provided useful information in the selection of training micrographs for this trial. The performance of this is shown in Table 4; an improvement over the previous model, as shown in Table 3. The precision and recall curves for this dataset are shown in FIG. 10B.

TABLE 4

Cross-Validation Studies on the Performance of a phosphor-GLUT1 Computer Model in Predicting Individual Outcomes[1-3]

| Outcome | Precision | Recall | Avg. Performance | N |
|---|---|---|---|---|
| Non-recurrent cancer | 97.2% | 94.8% | 94.7% | 182 |
| Recurrent cancer[4] | 89.5% | 94.4% | 91.9% | 87 |

[1]Experiments utilized a 512 × 512 EMCCD chip (Andor camera model DV-887).
[2]N is the number of micrographs. A total of 48 patients were used.
[3]Data from ipsilateral breast cancer recurrences are shown. Micrographs of solid DCIS lesions were not included.

Figure 12A:
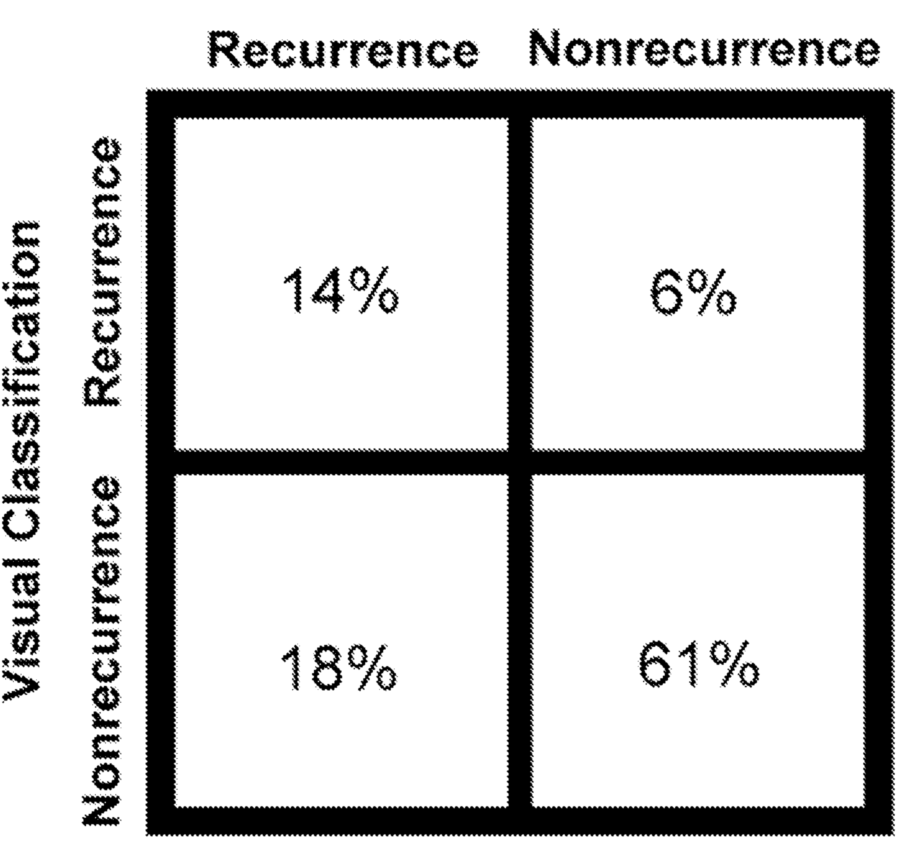
FIGS. 12A and 12B are confusion matrices of clinical outcome predictions using visual inspection of micrographs (FIG. 12A) and machine learning predictions (FIG. 10B). Observation-based classification of DCIS micrographs containing peripheral or non-peripheral PGLUT staining was correct (true positive+true negative) in 75% of the cases of the non-solid (cribriform, papillary, micropapillary, and comedo) DCIS cases. Machine-based classifications of DCIS micrographs yielded substantial improvements in the binary classification of patient outcomes.
Figure 12B:
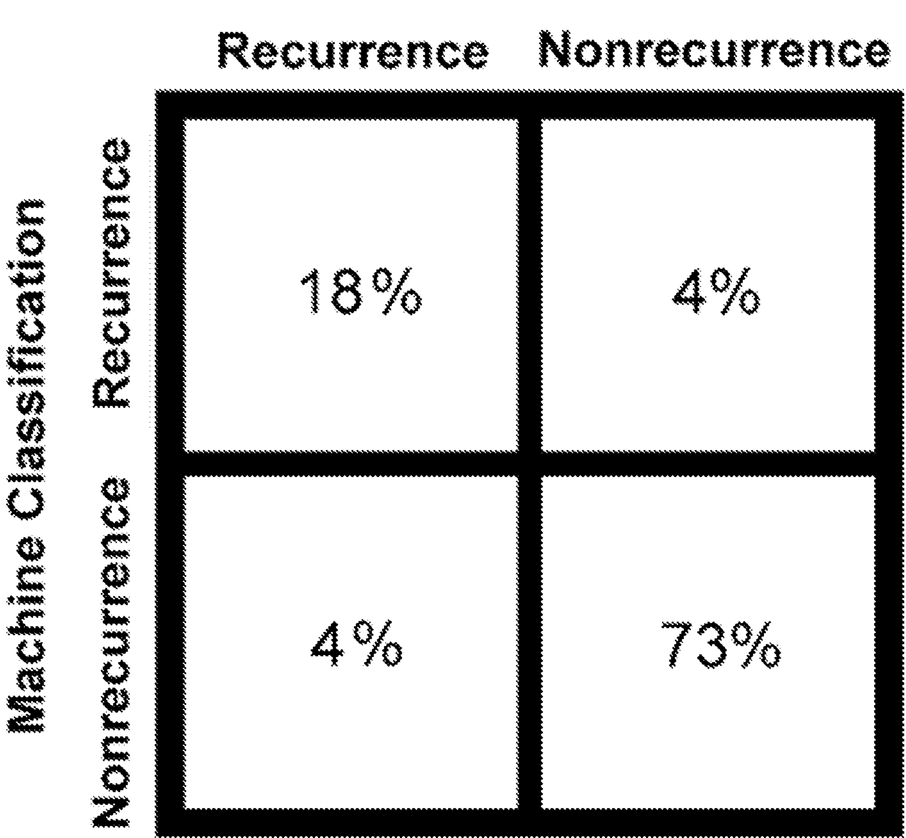

Using the computer model of Table 4, individual patient samples were evaluated. FIGS. 12A-B show confusion matrices for experiments utilizing visual inspection of the peripheral accumulation of biomarkers and for machine learning. Using the reported outcomes as an imperfect reference standard and a 50% threshold, the computed patient outcomes were: 73% true negatives, 18% true positives, 4% false positives, and 4% false negatives. Overall, these results compare favorably with other diagnostic tests of breast tissue. Sampling error may contribute to false negatives, for example, cells leading to a recurrence may be missed by sectioning and are elsewhere in the tissue block. The false negatives in these phospho-GLUT1 experiments were cross-checked with RhoA micrographs from the same tissue block (FIG. 6). Peripheral RhoA labeling was found in other sections from these patients, indicating that the false negatives were incorrectly judged; the samples were true positives missed in the test due to the limited number of micrographs. False negative can also be reduced by adjusting the threshold used in this determination. The false positives may have been due to the benefits of mastectomies. As all patients underwent mastectomies, the actual outcomes in the absence of surgery are unknown (i.e., "recurrent" patients who became "non-recurrent" after surgery); hence, false positives are expected among the patient outcomes.

REFERENCES

The following references, some of which are cited above by number, are herein incorporated by reference in their entireties.

1. L. J. Esserman, I. M. Thompson, B. Reid, Overdiagnosis and overtreatment in cancer: An opportunity for improvement. *JAMA* 310, 797-798 (2013).
2. C. Harding, F. Pompei, D. Burmistrov, H. G. Welch, R. Abebe, R. Wilson, Breast cancer screening, incidence, and mortality across US counties. *JAMA Intern. Med.* 175, 1483-1489 (2015).
3. E. Marshall, Breast cancer. Dare to do less. *Science* 343, 1454-1456 (2014).
4. Alpha-Tocopherol, Beta Carotene Cancer Prevention Study Group. The effect of vitamin E and beta carotene on the incidence of lung cancer and other cancers in male smokers. *N Engl J Med.* 330, 1029-1033 (1994).
5. K. Le Gal, M. X. Ibrahim, C. Wiel, V. I. Sayin, M. K. Akula, C. Karlsson, M. G. Dalin, L. M. Akyürek, P. Lindahl, J. Nilsson, M. O. Bergo, Antioxidants can increase melanoma metastasis in mice. *Sci Transl Med.* 7, 308re8 (2015).
6. J. M. Estrela, A. Ortega, E. Obrador, Glutathione in cancer biology and therapy. *Crit Rev Clin Lab Sci.* 43, 143-181 (2006).
7. J. Heo, K. W. Raines, V. Mocanu, S. L. Campbell. Redox regulation of RhoA. *Biochemistry.* 45, 14481-14489 (2006).
8. K. Kobayashi, H. Matsumoto, H. Matsuyama, N. Fujii, R. Inoue, Y. Yamamoto, K. Nagao. Clinical significance of CD44 variant 9 expression as a prognostic indicator in bladder cancer. *Oncol Rep.* 36, 2852-2860 (2016).
9. T. Ishimoto, O. Nagano, T. Yae, M. Tamada, T. Motohara, H. Oshima, M. Oshima, T. Ikeda, R. Asaba, H. Yagi, T. Masuko, T, Shimizu, T. Ishikawa, K. Kai, E. Takahashi, Y. Imamura, Y. Baba, M. Ohmura, M. Suematsu, H. Baba, H. Saya, CD44 variant regulates redox status in cancer cells by stabilizing the xCT subunit of system xc(−) and thereby promotes tumor growth. *Cancer Cell* 19, 387-400 (2011).
10. M. Van Geldermalsen, Q. Wang, R. Nagarajah, A. D. Marshall, A. Thoeng, D. Gao, W. Ritchie, Y. Feng, C. G. Bailey, N. Deng, K. Harvey, J. M. Beith, C. I. Selinger, S. A. O'Toole, J. E. Rasko, J. Hoist, ASCT2/SLC1A5 controls glutamine uptake and tumor growth in triple-negative basal-like breast cancer. *Oncogene* 35, 3201-8 (2016).
11. E. Babu, Y. D. Bhutia, S. Ramachandran, J. P. Gnanaprakasam, P. D. Prasad, M. Thangaraju, V. Ganapathy, Deletion of the amino acid transporter Slc6a14 suppresses tumour growth in spontaneous mouse models of breast cancer. *Biochem J.* 469, 17-23 (2015).
12. K. Shimizu, K. Kaira, Y. Tomizawa, N. Sunaga, O. Kawashima, N. Oriuchi, H. Tominaga, S. Nagamori, Y. Kanai, M. Yamada, T. Oyama, I. Takeyoshi, ASC amino-acid transporter 2 (ASCT2) as a novel prognostic marker in non-small cell lung cancer. *Br J Cancer* 110, 2030-9 (2014).
13. K. Kaira, Y. Sunose, K. Arakawa, T. Ogawa, N. Sunaga, K. Shimizu, H. Tominaga, N. Oriuchi, H. Itoh, S. Nagamori, Y. Kanai, A. Segawa, M. Furuya, M. Mori, T. Oyama, I. Takeyoshi. Prognostic significance of L-type amino-acid transporter 1 expression in surgically resected pancreatic cancer. *Br J Cancer* 107, 632-8 (2012).
14. A. Bansal, M. C. Simon. Glutathione metabolism in cancer progression and treatment resistance. *J Cell Biol.* 217, 2291-2298 (2018).
15. H. Q. Ju, Y. X. Lu, Q. N. Wu, J. Liu, Z. L. Zeng, H. Y. Mo, Y. Chen, T. Tian, Y. Wang, T. B. Kang, D. Xie, M. S. Zeng, P. Huang, R. H. Xu, Disrupting G6PD-mediated redox homeostasis enhances chemosensitivity in colorectal cancer. *Oncogene* 36, 6282-92 (2017)
16. I. M. Xu, R. K. Lai, S. H. Lin, A. P. Tse, D. K. Chiu, H. Y. Koh, C. T. Law, C. M. Wong, Z. Cai, C. C. Wong, I. O. Ng, Transketolase counteracts oxidative stress to drive cancer development. *Proc Natl Acad Sci USA* 113, E725-34 (2016).
17. M. Földi, E. Stickeler, L. Bau, O. Kretz, D. Watermann, G. Gitsch, G. Kayser, A. Zur Hausen A, J. F. Coy, Transketolase protein TKTL1 overexpression: A potential biomarker and therapeutic target in breast cancer. *Oncol Rep.* 17, 841-5 (2007).
18. E. A. Wellberg, S. Johnson, J. Finlay-Schultz, A. S. Lewis, K. L. Terrell, C. A. Sartorius, E. D. Abel, W. J. Muller, S. M. Anderson, The glucose transporter GLUT1 is required for ErbB2-induced mammary tumorigenesis. *Breast Cancer Res.* 18, 131 (2016).
19. C. Zhang, J. Liu, Y. Liang, R. Wu, Y. Zhao, X. Hong, M. Lin, H. Yu, L. Liu, A. J. Levine W. Hu, Z. Feng, Tumour-associated mutant p53 drives the Warburg effect. *Nat Commun.* 4, 2935 (2013).

20. K. O'Connor, M. Chen, Dynamic functions of RhoA in tumor cell migration and invasion. *Small GTPases* 4, 141-7 (2013).

21. D. Jeong, S. Park, H. Kim, C. J. Kim, T. S. Ahn, S. B. Bae, H. J. Kim, T. H. Kim, J. Im, M. S. Lee, H. Y. Kwon, M. J. Baek. RhoA is associated with invasion and poor prognosis in colorectal cancer. *Int J Oncol.* 48, 714-22 (2016).

22. M. E. Campanella, H. Chu, P. S. Low, Assembly and regulation of a glycolytic enzyme complex on the human erythrocyte membrane. *Proc Natl Acad Sci USA.* 102, 2402-7 (2005).

23. G. Daum, K. Keller, K. Lange, Association of glycolytic enzymes with the cytoplasmic side of the plasma membrane of glioma cells. *Biochim Biophys Acta.* 939, 277-81 (1988).

24. K. Uyeda, Interactions of glycolytic enzymes with cellular membranes. *Curr Topics Cell Regulation.* 33, 31-46 (1992).

25. L. Glass-Marmor, R. Beitner, Taxol (paclitaxel) induces a detachment of phosphofructokinase from cytoskeleton of melanoma cells and decreases the levels of glucose 1,6-bisphosphate, fructose 1,6-bisphosphate and ATP. *Eur J Pharmacol.* 370, 195-9 (1999).

26. W. N. Tian, J. N. Pignatare, R. C. Stanton, Signal transduction proteins that associate with the platelet-derived growth factor (PDGF) receptor mediate the PDGF-induced release of glucose-6-phosphate dehydrogenase from permeabilized cells. *J Biol Chem.* 269, 14798-805 (1994).

27. R. C. Stanton, J. L. Seifter, D. C. Boxer, E. Zimmerman, L. C. Cantley, Rapid release of bound glucose-6-phosphate dehydrogenase by growth factors. Correlation with increased enzymatic activity. *J Biol Chem.* 266, 12442-8 (1991).

28. R. C. Stanton, Glucose-6-phosphate dehydrogenase, NADPH, and cell survival. *IUBMB Life.* 64, 362-9 (2012).

29. M. Jain, D. A. Brenner, L. Cui, C. C. Lim, B. Wang, D. R. Pimentel, S. Koh, D. B. Sawyer, J. A. Leopold, D. E. Handy, J. Loscalzo, C. S. Apstein, R. Liao, Glucose-6-phosphate dehydrogenase modulates cytosolic redox status and contractile phenotype in adult cardiomyocytes. *Circ Res.* 93, e9-16 (2003).

30. A. L. Kindzelskii, J. B. Huang, T. Chaiworapongsa, R. M. Fahmy, Y. M. Kim, R. Romero, H. R. Petty, Pregnancy alters glucose-6-phosphate dehydrogenase trafficking, cell metabolism and oxidant release of maternal neutrophils. *J. Clin. Invest.* 110, 1801-1811 (2002).

31. A. L. Kindzelskii, J. B. Huang, T. Chaiworapongsa, R. M. Fahmy, Y. M. Kim, R. Romero, H. R. Petty, 6-Phosphogluconate dehydrogenase and glucose-6-phosphate dehydrogenase form complexes in human neutrophils and traffic to the centrosome in pregnant, but not non-pregnant, women. *J Immunol.* 172, 6373-6381 (2004).

32. J. B. Huang, J. Espinoza, R. Romero, H. R. Petty, Transaldolase is part of a supramolecular complex containing glucose-6-phosphate dehydrogenase in human neutrophils that undergoes retrograde trafficking during pregnancy. *Metabolism* 54, 1027-33 (2005).

33. M. Castellana, M. Z. Wilson, Y. Xu, P. Joshi, I. M. Cristea, J. D. Rabinowitz, Z. Gitai, N. S. Wingreen, Enzyme clustering accelerates processing of intermediates through metabolic channeling. *Nat Biotechnol.* 32, 1011-8 (2014).

34. P. Bauler, G. Huber, T. Leyh, J. A. McCammon, Channeling by proximity: the catalytic advantages of active site colocalization using Brownian dynamics. *J Phys Chem Lett.* 1:1332-1335 (2010).

35. G. Adam, M. Delbruck, Reduction of dimensionality in biological diffusion processes. In: *Structural Chemistry and Molecular Biology*, (edited by A. Rich and N. Davidson (Freeman, San Francisco, CA) pp. 198-215 (1968).

36. P. H. von Hippel, O. G. Berg, Facilitated target location in biological systems. *J Biol Chem.* 264, 675-8 (1989).

37. Kusama, T. Mukai M, Iwasaki T, Tatsuta M, Matsumoto Y, Akedo H, Nakamura H. Inhibition of epidermal growth factor-induced RhoA translocation and invasion of human pancreatic cancer cells by 3-hydroxy-3-methylglutaryl-coenzyme A reductase inhibitors. *Cancer Res.* 61, 4885-91 (2001).

38. Lee, E. E. Ma J, Sacharidou A, Mi W, Salato V K, Nguyen N, Jiang Y, Pascual J M, North P E, Shaul P W, Mettlen M, Wang R C. A protein kinase C phosphorylation motif in GLUT1 affects glucose transport and is mutated in GLUT1 deficiency syndrome. *Mol Cell.* 58, 845-53 (2015).

39. C. Pardo-Pastor, F. Rubio-Moscardo, M. Vogel-González, S. A. Serra, A. Afthinos, S. Mrkonjic, O. Destaing, J. F. Abenza, J. M. Fernández-Fernández, X. Trepat, C. Albiges-Rizo, K. Konstantopoulos, M. A. Valverde. Piezo2 channel regulates RhoA and actin cytoskeleton to promote cell mechanobiological responses. *Proc Natl Acad Sci USA.* 115, 1925-1930 (2018).

40. F. Broders-Bondon, T. H. Nguyen Ho-Bouldoires, M. E. Fernandez-Sanchez, E. Farge, Mechanotransduction in tumor progression: The dark side of the force. *J Cell Biol.* 217, 1571-1587 (2018).

41. P. Lochman, T. Adam, D. Friedecký, E. Hlídková, Z Skopková, High-throughput capillary electrophoretic method for determination of total aminothiols in plasma and urine. *Electrophoresis.* 24, 1200-7 (2003).

42. M. H. Zarka, W. J. Bridge, Oral administration of γ-glutamylcysteine increases intracellular glutathione levels above homeostasis in a randomised human trial pilot study. *Redox Biol.* 11, 631-636 (2017).

43. A. A. Stark, N. Porat, G. Volohonsky, A. Komlosh, E. Bluvshtein, C. Tubi, P. Steinberg, The role of gamma-glutamyl transpeptidase in the biosynthesis of glutathione. *Biofactors.* 17, 139-49 (2003).

44. M. E. Anderson, A. Meister, Transport and direct utilization of gamma-glutamylcyst(e)ine for glutathione synthesis. *Proc Natl Acad Sci USA.* 80, 707-11 (1983).

45. G. Ferguson, W. Bridge, Glutamate cysteine ligase and the age-related decline in cellular glutathione: The therapeutic potential of γ-glutamylcysteine. *Arch Biochem Biophys.* 593, 12-23 (2016).

46. P. G. Richman, A. Meister, Regulation of gamma-glutamyl-cysteine synthetase by nonallosteric feedback inhibition by glutathione. *J Biol Chem.* 250, 1422-6 (1975).

47. M. Wang, P. J. Casey, Protein prenylation: unique fats make their mark on biology. *Nat Rev Mol Cell Biol.* 17, 110-22 (2016).

48. J. Kapuscinski, DAPI: a DNA-specific fluorescent probe. *Biotech Histochem.* 70, 220-233 (1995).

49. A. J. Clark, H. R. Petty, Protocol for biomarker ratio imaging microscopy with specific application to ductal carcinoma in situ of the breast. *Frontiers in Cell and Developmental Biology* 4, 120 (2016).

50. A. J. Clark, H. R. Petty, Identification of lesion subtypes in biopsies of ductal carcinoma in situ of the breast using biomarker ratio imaging microscopy. *Scientific Rep.* 6, 27039 (2016).

51. I. Campbell, Chi-squared and Fisher-Irwin tests of two-by-two tables with small sample recommendations. *Stat Med* 26, 3661-75 (2007).

52. Shorten, C., Khoshgoftaar, T. M. A survey on image data augmentation for deep learning. *J Big Data* 6:60, 1-48 (2019).

53. T. Saito, M. Rehmsmeier, The precision-recall plot is more informative than the ROC plot when evaluating binary classifiers on imbalanced datasets. PLoS One 10, e0118432 (2015).

The invention claimed is:

1. A method comprising:

determining intracellular localization of at least one biomarker for breast cancer recurrence in a sample comprising breast cancer cells from a subject, wherein the biomarker for cancer recurrence is selected from serine-226 phosphorylated glucose transporter type 1 (phospho-GLUT1), transketolase-like protein-1, glutathione synthetase, GTP-loaded RhoA, and RhoA, and wherein determining intracellular localization comprises: (1) immunostaining the sample with a primary antibody directed to the biomarker for breast cancer recurrence, and (2) imaging the sample; and predicting cancer recurrence in the subject, wherein peripheral intracellular localization of the at least one biomarker indicates recurrent cancer.

2. The method of claim 1, wherein the primary antibody is detected with a secondary antibody comprising a detectable label.

3. The method of claim 1, wherein imaging the sample comprises fluorescence microscopy.

4. The method of claim 1, wherein the breast cancer comprises ductal carcinoma in situ of the breast, lobular carcinoma in situ, atypical ductal hyperplasia, or atypical lobular hyperplasia.

5. The method of claim 1, wherein the breast cancer recurrence is ipsilateral breast cancer recurrence.

6. The method of claim 1, wherein the sample comprises a formalin-fixed paraffin-embedded breast cancer tissue sample or a breast cancer metastases tissue or cell sample.

7. The method of claim 1, further comprising treating a subject predicted to have breast cancer recurrence with surgery.

8. The method of claim 1, further comprising treating a subject predicted to have breast cancer recurrence with administration of inhibitors to enzyme or transporter accumulation at plasma membrane.

9. The method of claim 8, wherein the inhibitors to enzyme accumulation at plasma membrane comprise colchicine, paclitaxel, a calmodulin antagonist, a prenylation inhibitor, an anesthetic, or combinations thereof.

* * * * *